US011531033B2

(12) United States Patent
Dervieux et al.

(10) Patent No.: US 11,531,033 B2
(45) Date of Patent: Dec. 20, 2022

(54) METHODS FOR TREATING AND DIAGNOSING SYSTEMIC LUPUS ERYTHEMATOSUS

(71) Applicant: Exagen Inc., Vista, CA (US)

(72) Inventors: Thierry Dervieux, San Diego, CA (US); Derren Barken, Vista, CA (US)

(73) Assignee: Exagen Inc., Vista, CA (US)

( * ) Notice: Subject to any disclaimer, the term of this patent is extended or adjusted under 35 U.S.C. 154(b) by 0 days.

(21) Appl. No.: 14/767,461

(22) PCT Filed: Mar. 13, 2014

(86) PCT No.: PCT/US2014/025264
§ 371 (c)(1),
(2) Date: Aug. 12, 2015

(87) PCT Pub. No.: WO2014/151238
PCT Pub. Date: Sep. 25, 2014

(65) Prior Publication Data
US 2015/0369824 A1 Dec. 24, 2015

Related U.S. Application Data

(60) Provisional application No. 61/792,284, filed on Mar. 15, 2013.

(51) Int. Cl.
*G01N 33/564* (2006.01)
*G01N 33/68* (2006.01)
(52) U.S. Cl.
CPC ....... *G01N 33/6893* (2013.01); *G01N 33/564* (2013.01); *G01N 33/6854* (2013.01); *G01N 2800/104* (2013.01); *G01N 2800/24* (2013.01); *G01N 2800/50* (2013.01); *G01N 2800/52* (2013.01); *G01N 2800/56* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 7,361,517 B2 | 4/2008 | Ahearn et al. | |
| 7,390,631 B2 | 6/2008 | Ahearn et al. | |
| 7,585,640 B2 | 9/2009 | Ahearn et al. | |
| 7,588,905 B2 | 9/2009 | Ahearn et al. | |
| 8,080,382 B2 | 12/2011 | Ahearn et al. | |
| 8,126,654 B2 | 2/2012 | Ahearn et al. | |
| 9,804,156 B2 * | 10/2017 | Ramachandran | G01N 33/564 |
| 10,132,813 B2 | 11/2018 | Dervieux et al. | |
| 2006/0071797 A1 | 4/2006 | Rosenfeld et al. | |
| 2007/0148704 A1 | 6/2007 | Klause et al. | |
| 2010/0233752 A1 | 9/2010 | Ahearn et al. | |
| 2011/0177531 A1 | 7/2011 | Dervieux et al. | |
| 2019/0025326 A1 | 1/2019 | Dervieux et al. | |

FOREIGN PATENT DOCUMENTS

| | | |
|---|---|---|
| EP | 2 336 769 A1 | 6/2011 |
| WO | WO-2007/039280 A1 | 4/2007 |
| WO | WO-2007/117141 A1 | 10/2007 |
| WO | WO-201/0045611 A2 | 4/2010 |
| WO | WO-201/0045611 A3 | 4/2010 |
| WO | WO-2011/047337 A2 | 4/2011 |
| WO | WO-2011/047337 A3 | 4/2011 |
| WO | 2012/109592 | 8/2012 |

OTHER PUBLICATIONS

Aarden, L.A., et al. N.Y. Annal. Acad. Sci. 1975;254:505-515. (1975).*
Kalunian et al., "Measurement of cell-bound complement activation products enhances diagnostic performance in systemic lupus erythematosus," Arthritis & Rheumatism, 64(12):4040-47 (Dec. 2012).
Putterman et al., "An Assay Panel Combining Cell Bound Complement Activation Products With Autoantibodies to Extractable Nuclear Antigens and Mutated Citrullinated Vimentin Helps with the Differential Diagnosis of Systemic Lupus Erythematosus," Arthritis & Rheumatism, 65(S10):S1078 (Oct. 2013).
Amissah-Arthur, M.B. et. al. (2010). "Contemporary treatment of systemic lupus erythematosus: an update for clinicians," *Ther Adv Chronic Dis* 1(4):163-175.
Bang, H. et al. (Aug. 2007). "Mutation and citrullination modifies vimentin to a novel autoantigen for rheumatoid arthritis," *Arthritis Rheum* 56(8):2503-2511.
Bastian, H.M. et al. (2002). "Systemic lupus erythematosus n three ethnic groups. XII. Risk factors for lupus nephritis after diagnosis," *Lupus* 11(3):152-160.
Batal,I, et al. (Jan. 2012, e-published Sep. 29, 2011). "Prospective assessment of C4d deposits on circulating cells and renal tissues in lupus nephritis: a pilot study," *Lupus* 21(1):13-26.
Clough, J.D. et al. (Feb. 1984). "Weighted criteria for the diagnosis of systemic lupus erythematosus," *Arch Intern Med* 144(2):281-285.
Corvetta, A. et al., (Jul. 1991) "Low Number of complement C3blC4b receptors (CR) erythrocytes from patients with essential mixed cryglobulinemia, systemic lupus erythematosus and rheumatoid arthritis: relationship with disease activity anticardolipin antibodies, complement activation and therapy," *J. Rheumatol*, 18(7):1021-1025.
Costenbader, K.H. et al. (Dec. 2002). "Defining lupus cases for clinical studies: the Boston weighted criteria for the classification of systemic lupus erythematosus," *J Rheumatol* 29(12)2545-2550.
Durcan, L. et al. (Nov. 2015, e-published Oct. 1, 2015). "Hydroxychloroquine Blood Levels in Systemic Lupus Erythematosus: Clarifying Dosing Controversies and Improving Adherence," *J Rheumatol* 42(11):2092-2097.

(Continued)

*Primary Examiner* — G. R. Ewoldt
(74) *Attorney, Agent, or Firm* — Mintz, Levin, Cohn, Ferris, Glovsky and Popeo, P.C.

(57) ABSTRACT

Methods and reagents for diagnosing, prognosing, and treating systemic lupus erythematosus (SLE) are disclosed, involving calculating an SLE risk score for a subject based on a level of each of an erythrocyte C4d (EC4d) marker, a B-cell C4d (BC4d) marker, antinuclear antibodies (ANA), anti-Smith antibodies (anti-Sm) and optional rule-out markers (SS-B/La, Scl-70, Jo-1, CENP, MCV).

14 Claims, 2 Drawing Sheets

(56) References Cited

OTHER PUBLICATIONS

Egner, W. (Jun. 2000). "The use of laboratory tests in the diagnosis of SLE," *J Clin Pathol* 53(6):424-432.

Helmick, C.G. et al. (Jan. 2008). "Estimates of the prevalence of arthritis and other rheumatic conditions in the United States. Part I," *Arthritis Rheum* 58(1):15-25.

Iida, K. et al., (May 1, 1982). "Complement receptor (CR1) deficiency in erythrocytes from patients with systemic lupus mythematosus," *J. Exp Med* 155(5):1427-1438.

Kalunian, K.C. et al. (Nov. 6, 2011) "The contribution of cell bound complement activation products to the diagnosis of Systemic Lupus Erythematosus," Arthritis & Rheumatism, 63: 1-2, abstract supplement.

Kao A.H. et al. (Mar. 2010). "Erythrocyte C3d and C4d for monitoring lisease activity in systemic lupus erythematosus," *Arthritis and Rheumatism* 62(3):837-844.

Liu, C.C. et al. (Aug. 2009). Lymphocyte-bound complement activation products as biomarkers for diagnosis of systemic lupus erythematosus. *Clin Transl Sci* 2(4):300-308.

Manderson, A.P. et al. (2004). "The role of complement in the development of systemic lupus erythematosus," *Annu Rev Immunol* 22:431-456.

Manzi, S. et al. (Nov. 2004). "Measurement of erythrocyte C4d and aomplement receptor 1 in systemic lupus erythematosus," *Arthritis Rheum* 50(11):3596-3604.

Manzi, S. et al., (2004) New insights into complement: a mediator of injury and marker of disease activity in systemic lupus erythematosus, *Lupus* 13(5):298-303.

Mok, C.C. et al. (Sep. 2016, e-published Jul. 27, 2016). "Hydroxychloroquine Serum Concentrations and Flares of Systemic Lupus Erythematosus: A Longitudinal Cohort Analysis," Arthritis Care Res 68(9):1295-1302.

Navratil, J.S. et al. (Feb. 2006). "Platelet C4d is highly specific for systemic lupus erythematosus," *Arthritis Rheum* 54(2):670-674.

Park, H.A. (Apr. 2013). An introduction to logistic regression: from basic concepts to interpretation with particular attention to nursing domain, *J Korean Acad Nurs* 43(2):154-164.

Petri, M. et al. (2004). "Classification criteria for systemic lupus erythematosus: a review," *Lupus* 13(11):829-837.

Poulsom, H. et al. (2008). "Antibodies to Citrullinated Vimentin are a Specific and Sensitive Marker for the Diagnosis of Rheumatoid Arthritis," *Clinic Rev Aller Immunol*, 34:4-10.

Putterman, C. et al., (Dec. 3, 2013). "Multicenter study in the An Assay Panel Combining Cell Bound Complement Activation Products with Autoantibodies to Extractable Nuclear Antigens and Mutated Citrullinated Vimentin Helps with the Differential Diagnosis of Systemic Lupus Erythematosus," 2013 ACR/ARHP Annual Meeting, 5 pages.

Rahman, A. et al. (Feb. 28, 2008). "Systemic lupus erythematosus," *N Engl J Med* 358(9):929-939.

Ross, G.D. et al. (Sep. 1985). "Disease-associated loss of erythrocyte complement receptors CR1, C3b receptors) in patients with systemic lupus erythematosus and other diseases involving autoantibodies and/or complement activation," *J. Immunol*, 135(3):2005-2014.

Singh, V. et al. (Oct. 2008, e-published Aug. 15, 2008). "Erythrocyte C4d and complement receptor 1 in systemic lupus erythematosus," *J Rheumatol* 35(10):1989-1993.

Smith, E.L. et al. (1999). "The American College of Rheumatology criteria for the classification of systemic lupus erythematosus: strengths, weaknesses, and opportunities for improvement," *Lupus* 8(8):586-595.

Sperandei, S. et al. (2014). "Undersanding Logistic Regression Analysis," Biochemia Medica 24(1):12-18.

Tan, E.M. et al. (Nov. 1982). "The 1982 revised criteria for the classification pf systemic lupus erythematosus," *Arthritis Rheum* 25(11):1271-1277.

Yang, D.H. et al. (Sep. 2009, e-published Jun. 24, 2009). "Usefulness of erythrocyte-bound C4d as a biomarker to predict disease activity in patients with systemic lupus erythematosus," *Rheumatology (Oxford)* 48(9):1083-1087.

\* cited by examiner

METHODS FOR TREATING AND DIAGNOSING SYSTEMIC LUPUS ERYTHEMATOSUS

CROSS REFERENCE TO RELATED APPLICATIONS

This application is a Section 371 US National Phase of International Application No. PCT/US2014/025264 filed Mar. 13, 2014, which claims priority to U.S. Application No. 61/792,284 filed Mar. 15, 2013, incorporated by reference herein in its entirety.

BACKGROUND

Systemic Lupus Erythematosus (SLE) is an autoimmune disease, characterized by the production of unusual autoantibodies in the blood. These autoantibodies bind to their respective antigens, forming immune complexes which circulate and eventually deposit in tissues. This immune complex deposition causes chronic inflammation and tissue damage.

The precise reason for the abnormal autoimmunity that causes lupus is not known. Inherited genes, viruses, ultraviolet light, and drugs may all play some role. Genetic factors increase the tendency of developing autoimmune diseases, and autoimmune diseases such as lupus, rheumatoid arthritis, and immune thyroid disorders are more common among relatives of patients with lupus than the general population. Some scientists believe that the immune system in lupus is more easily stimulated by external factors like viruses or ultraviolet light. Sometimes, symptoms of lupus can be precipitated or aggravated by only a brief period of sun exposure.

Since patients with SLE can have a wide variety of symptoms and different combinations of organ involvement, no single test establishes the diagnosis of SLE. To help doctors improve the accuracy of diagnosis of SLE, eleven criteria were established by the American Rheumatism Association. These eleven criteria are closely related to the variety of symptoms observed in patients with SLE. When a person has four or more of these criteria, the diagnosis of SLE is strongly suggested. However, some patients suspected of having SLE may never develop enough criteria for a definite diagnosis. Other patients accumulate enough criteria only after months or years of observation. Nevertheless, the diagnosis of SLE may be made in some settings in patients with only a few of these classical criteria. Of these patients, a number may later develop other criteria, but many never do. The eleven criteria conventionally used for diagnosing SLE are:

1—malar over the cheeks of the face or "butterfly" rash
2—discoid skin rash: patchy redness that can cause scarring
3—photosensitivity: skin rash in reaction to sunlight exposure
4—mucus membrane ulcers: ulcers of the lining of the mouth, nose or throat
5—arthritis: two or more swollen, tender joints of the extremities
6—pleuritis/pericarditis: inflammation of the lining tissue around the heart or lungs, usually associated with chest pain with breathing
7—kidney abnormalities: abnormal amounts of urine protein or clumps of cellular elements called casts
8—brain irritation: manifested by seizures (convulsions) and/or psychosis
9—blood count abnormalities: low counts of white or red blood cells, or platelets
10—immunologic disorder: abnormal immune tests include anti-dsDNA or anti-Sm (Smith) antibodies, false positive blood tests for syphilis, anticardiolipin antibodies, lupus anticoagulant, or positive LE prep test, and
11—antinuclear antibody: positive ANA antibody testing Although the criteria serve as useful reminders of those features that distinguish lupus from other related autoimmune diseases, they are unavoidably fallible. Determining the presence or absence of the criteria often requires interpretation. If liberal standards are applied for determining the presence or absence of a sign or symptom, one could easily diagnose a patient as having lupus when in fact they do not. Similarly, the range of clinical manifestations in SLE is much greater than that described by the eleven criteria and each manifestation can vary in the level of activity and severity from one patient to another. To further complicate a difficult diagnosis, symptoms of SLE continually evolve over the course of the disease. New symptoms in previously unaffected organs can develop over time. Because conventionally there is no definitive test for lupus, it is often misdiagnosed.

Monitoring disease activity is also problematic in caring for patients with lupus. Lupus progresses in a series of flares, or periods of acute illness, followed by remissions. The symptoms of a flare, which vary considerably between patients and even within the same patient, include malaise, fever, symmetric joint pain, and photosensitivity (development of rashes after brief sun exposure). Other symptoms of lupus include hair loss, ulcers of mucous membranes and inflammation of the lining of the heart and lungs which leads to chest pain.

Red blood cells, platelets and white blood cells can be targeted in lupus, resulting in anemia and bleeding problems. More seriously, immune complex deposition and chronic inflammation in the blood vessels can lead to kidney involvement and occasionally failure requiring dialysis or kidney transplantation. Since the blood vessel is a major target of the autoimmune response in lupus, premature strokes and heart disease are not uncommon. Over time, however, these flares can lead to irreversible organ damage.

SUMMARY OF THE INVENTION

In a first aspect, the invention provides methods for treating a subject at risk of Systemic Lupus Erythematosus (SLE), comprising
(a) calculating an SLE risk score for a subject based on a level of each of the following primary markers in a biological sample from a subject at risk of having SLE:
(I) an erythrocyte C4d (EC4d) marker;
(II) a B-cell C4d (BC4d) marker; and
(III) anti-nuclear antibodies (ANA);
wherein the subject is at risk of having SLE, and wherein the subject is negative for SLE based on individual levels of the EC4d marker, the BC4d marker, anti-Smith (anti-Sm) antibodies, and double stranded DNA antibodies (anti-dsDNA); and
(b) treating the subject for SLE or another disease based at least in part on the SLE risk score.

In another aspect, the invention provides methods for diagnosing a likelihood of SLE in a subject at risk thereof, comprising
(a) determining that a subject at risk of SLE is negative for SLE based on individual levels of the EC4d marker, the BC4d marker, anti-Smith (anti-Sm) antibodies, and double stranded DNA antibodies (anti-dsDNA); and (b) calculating an SLE risk score based on a level of each of the following primary markers in a biological sample from a subject at risk of having SLE:

(I) an erythrocyte C4d (EC4d) marker;
(II) a B-cell C4d (BC4d) marker; and
(III) anti-nuclear antibodies (ANA);

wherein the risk score indicated a likelihood of the subject having SLE.

In one embodiment of the methods, the method further comprises determining in a biological sample from the subject a level of one, two, three, or all four rule-out markers selected from the group consisting of an SS-B (La) marker, an Scl-70 marker, a Jo-1 marker, and a CENP marker, and wherein the calculating the SLE risk score comprises calculating the SLE risk score based on the levels of each of the primary markers and the one or more rule-out markers.

In another embodiment, the method further comprises determining in a biological sample from the subject a level of an MCV marker, and wherein the calculating the SLE risk score comprises calculating the SLE risk score based on the levels of each of the primary markers the one or more rule-out markers, and the MCV marker.

In a further embodiment, calculating the SLE risk score comprises adjusting the level of one or more of the primary markers by one or more transformation analyses. In one such embodiment, the one or more transformation analyses comprise logistic regression analysis, and wherein the logistic regression analysis comprises (i) adjusting the level of each of the primary markers to produce a weighted score for each primary marker, and (ii) combining the weighted score for each primary marker to generate the SLE risk score.

In another embodiment, calculating the SLE risk score comprises adjusting the level of one, two, three, or all four of the rule-out markers by one or more transformation analyses. In one such embodiment, the one or more transformation analyses comprise logistic regression analysis, and wherein the logistic regression analysis comprises (i) adjusting the level of each of the primary markers and the level of each of the one two, three, or all four rule-out markers to produce a weighted score for primary markers and the one two, three, or all four rule-out markers, and (ii) combining the weighted score for each primary marker and the one two, three, or all four rule-out markers to generate the SLE risk score.

In a further embodiment, the SLE risk score is calculated by (a) determining the natural log of net mean fluorescence intensity determined by fluorescence activated cell sorting (FACS) for EC4d and BC4d;

(b) determining whether ANA is negative (value of 0), moderately positive (value of 1), or strong positive (value of 2) based on a predetermined threshold value;

(c) determining whether any of the rule out markers fall above a predetermined threshold value and thus are positive (value of 1), or that none of the rule out markers fall above the predetermined threshold value and thus are all negative (value of 0); and (d) combining the values determined in (a)-(c) to arrive at the SLE risk score.

DETAILED DESCRIPTION OF THE INVENTION

Figure 1:
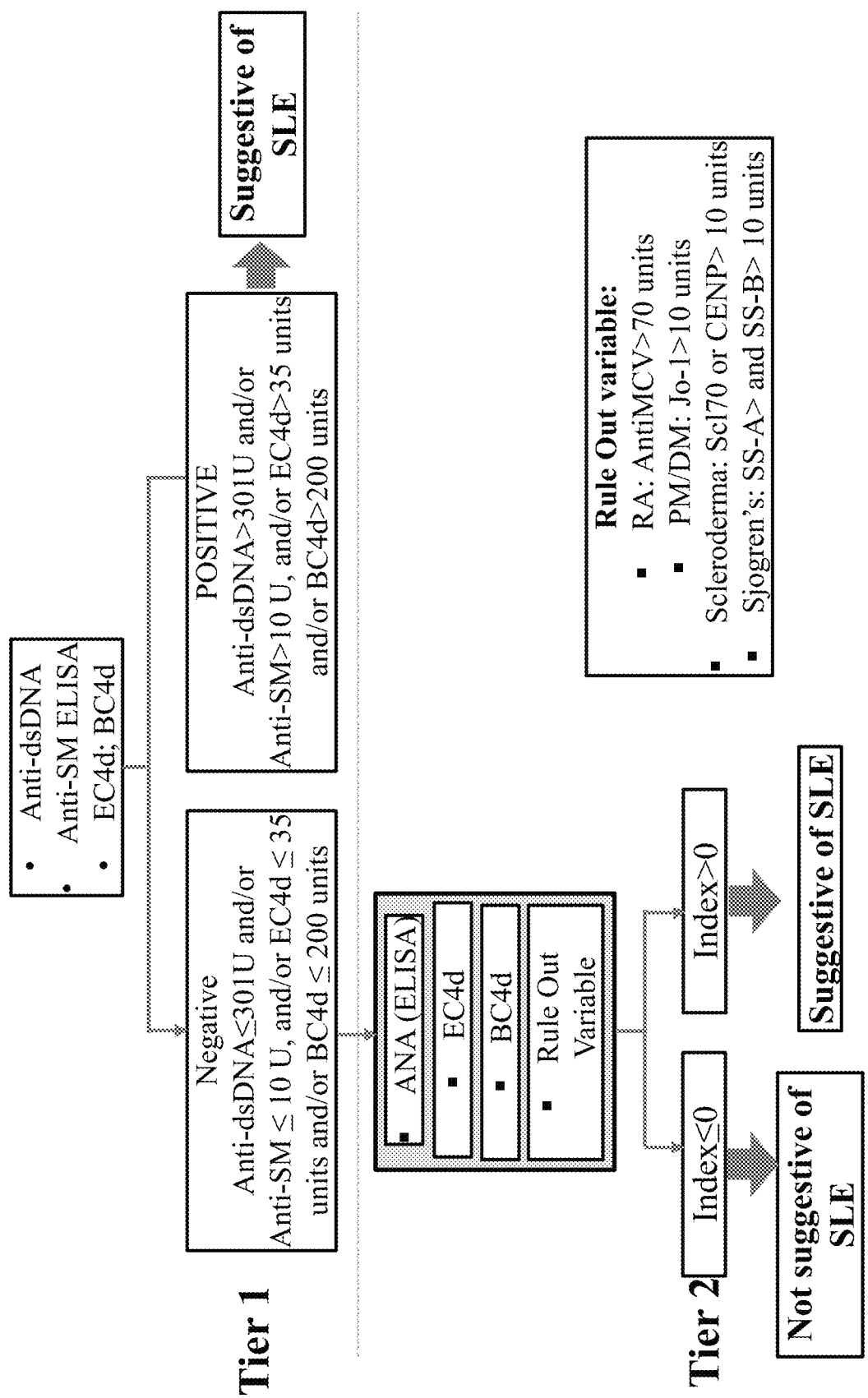
FIG. 1 is a flow chart illustrating an embodiment of the methods of the invention for diagnosing SLE based on blood sample levels of cell-based complement activation products containing two detection tiers.

All of the references cited herein are incorporated by reference. All embodiments disclosed herein can be combined with one or more other embodiments in the same or different aspect of the invention, unless the context clearly indicates otherwise.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Additionally, the words "herein," "above," and "below" and words of similar import, when used in this application, shall refer to this application as a whole and not to any particular portions of this application. As used herein, the singular forms "a", "an" and "the" include plural referents unless the context clearly dictates otherwise. "And" as used herein is interchangeably used with "or" unless expressly stated otherwise.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments.

In a first aspect, the present invention provides methods for treating a subject at risk of Systemic Lupus Erythematosus (SLE), comprising (a) calculating an SLE risk score (also referred to herein as an "index score') for a subject based on a level of each of the following primary markers in a biological sample from a subject at risk of having SLE:

(I) an erythrocyte C4d (EC4d) marker;
(II) a B-cell C4d (BC4d) marker; and
(III) anti-nuclear antibodies (ANA);

wherein the subject is at risk of having SLE, and wherein the subject is negative for SLE based on individual levels of the EC4d marker, the BC4d marker, anti-Smith (anti-Sm) antibodies, and double stranded DNA antibodies (anti-dsDNA); and (b) treating the subject for SLE or another disease based at least in part on the SLE risk score.

In a second aspect, the present invention provides methods for diagnosing a likelihood of SLE in a subject at risk thereof, comprising (a) determining that a subject at risk of SLE is negative for SLE based on individual levels of the EC4d marker, the BC4d marker, anti-Smith (anti-Sm) antibodies, and double stranded DNA antibodies (anti-dsDNA); and (b) calculating an SLE risk score based on a level of each of the following primary markers in a biological sample from a subject at risk of having SLE:
  (I) an erythrocyte C4d (EC4d) marker;
  (II) a B-cell C4d (BC4d) marker; and
  (III) anti-nuclear antibodies (ANA);
wherein the risk score indicated a likelihood of the subject having SLE.

The methods of the invention provide improvements in diagnosing and treating Systemic Lupus Erythematosus (SLE) compared to prior art methods. In one embodiment of either aspect, the methods further comprise determining in a biological sample from the subject a level of one or more (e.g., 1, 2, 3, or all 4) rule-out markers selected from the group consisting of a Sjögren syndrome type B antigen (SS-B (La)) marker, an Scl-70 marker (topoisomerase I), a Jo-1 marker, and a centromere B protein (CENP) marker, wherein the calculating the SLE risk score comprises calculating the SLE risk score based on the levels of each of the primary markers and the one or more rule-out markers. In this embodiment, the specificity for SLE diagnosis is greatly improved compared to prior art methods.

The marker may be any suitable marker, such as antibodies in the biological sample against the one or more rule-out markers. For example, a Jo-1 marker could be an Anti-Jo-1 antibody, an SS-B (La) marker could be an anti SS-B (La) antibody, an Scl-70 marker could be an anti-Scl-70 antibody, and a CENP marker could be an anti-CENP antibody. In a further embodiment, the rule out markers may further include an MCV (mutated citrullinated vimentin) marker, such as an anti-MCV antibody.

Probes and assays for measuring levels of each of these markers and normal levels in various tissue samples are known to those of skill in the art, and kits for making such measurements are available from a wide variety of manufactures, including but not limited to those mentioned in the examples that follow.

In another embodiment of either aspect, calculating the SLE risk score comprises adjusting the level of one or more of the primary markers by one or more transformation analyses. Any such transformation analysis may be used, including but not limited to logistic regression analysis. In such embodiment, the logistic regression analysis may comprise:
  (i) adjusting the level of each of the primary markers to produce a weighted score for each primary marker, and
  (ii) combining the weighted score for each primary marker to generate the SLE risk score.

In another embodiment, calculating the SLE risk score comprises adjusting the level of the one or more of the primary markers and the level of the one or more (1, 2, 3, or all 4) rule-out markers by one or more transformation analyses. In such an embodiment the one or more transformation analyses may comprise logistic regression analysis comprising
  (i) adjusting the level of each of the primary markers and the level of each of the one or more rule-out markers to produce a weighted score for primary markers and the one or more rule-out markers, and
  (ii) combining the weighted score for each primary marker and the one or more rule-out markers to generate the SLE risk score.

$$\text{Index}=-5.2626+0.9877 \times ANAComp+[0.2955 \times \log(EC4d)+1.0260 \times \log(BC4d)]-2.4944 \times SpecComp.$$

In such an embodiment, the mean fluorescence intensity (for example, output from flow cytometer) is measured for (EC4d) and (BC4d) and the log is taken. "ANA20" refers to positivity; above a threshold number of ANA units per ml of sample ANA20=1; below the threshold number of units per ml ANA20=0. As will be understood by those of skill in the art, the "threshold" for determining a marker as "positive" or not may differ from one manufacturer/assay to another, but can be readily determined by those of skill in the art. The "RuleOut" is determined as follows: it is 1 if the assay is positive for any "RuleOut" marker, and 0 if negative for all "RuleOut" markers.

In one embodiment, the SLE risk score can be calculated by
  (a) determining the natural log of net mean fluorescence intensity (determined by fluorescence activated cell sorting (FACS)) for EC4d and BC4d;
  (b) determining whether ANA is negative (value of 0), moderately positive (value of 1), or strong positive (value of 2) based on a predetermined threshold value (such as thresholds determined by kit manufacturer or end user);
  (c) determining whether any of the rule out markers fall above a predetermined threshold value and thus are positive (value of 1), or that none of the rule out markers fall above the predetermined threshold value and thus are all negative (value of 0); and
  (d) combining the values determined in (a)-(c) to arrive at the SLE risk score, optionally comprises adjusting the level of the one or more of the markers by one or more transformation analyses.

In a further embodiment, determining the BC4d marker level comprises determining the level of BC4d on the surface of B lymphocytes and determining the EC4d marker level comprises determining the level of EC4d on the surface of erythrocytes. For example, determining the BC4d marker level may comprise determining the level of BC4d in a cell or tissue extract comprising B lymphocytes, and determining the EC4d marker level may comprise determining the level of EC4d in a cell or tissue extract comprising erythrocytes. In a further embodiment, the level of the BC4d marker and the level of the EC4d marker is determined using an antibody specific for C4d, such as those known in the art.

The present invention provides improved methods for the diagnosis and for treating subjects at risk of having Systemic Lupus Erythematosus (SLE) that appear to be negative base on initial assessment using levels of individual markers.

The subject is preferably a human subject (adult or pediatric). SLE is an autoimmune disease, characterized by the production of unusual autoantibodies in the blood. These autoantibodies bind to their respective antigens, forming immune complexes which circulate and eventually deposit in tissues. Subjects at risk of SLE may have symptoms including, but not limited to, malaise, fever, chronic inflammation, tissue damage; malar over the cheeks of the face or "butterfly" rash; discoid skin rash: patchy redness that can cause scarring; photosensitivity: skin rash in reaction to sunlight exposure, mucus membrane ulcers: ulcers of the lining of the mouth, nose or throat; arthritis: two or more swollen, tender joints of the extremities; pleuritis/pericarditis: inflammation of the lining tissue around the heart or lungs, chest pain with breathing; hair loss; kidney abnormalities: abnormal amounts of urine protein or clumps of cellular elements called casts; brain irritation: manifested by seizures (convulsions) and/or psychosis; blood count abnormalities; immunologic disorder: and false positive blood tests for syphilis.

As used herein, the "biological sample" is obtained from the subject's body. Any suitable biological sample from the subject may be used. Particularly suitable samples for use in the methods of the invention are blood samples, biopsy samples, including but not limited to kidney biopsies. In one embodiment, serological markers (such as an ANA, CENP, Jo-1, La/SS-B, and SCl-70 marker) are obtained from a blood sample, while EC4d, PC4d, ECR1, and/or BC4d markers are those deposited on circulating blood cells.

Blood samples are preferably treated with EDTA (ethylenediaminetetraacetate) to inhibit complement activation. Samples can be maintained at room temperature or stored at 4° C. In some embodiments, a whole blood sample may be fractionated into different components. For instance, in one embodiment, red blood cells are separated from other cell types in the sample by differential centrifugation. Analysis of complement activation products bound to erythrocytes (e.g., EC4d and ECR1) can be performed on the isolated red blood cells. In some embodiments, the white blood cells are isolated from other components of the blood sample. For example, white blood cells (the buffy coat) can be isolated from plasma and from red blood cells by centrifugation. Each type of white blood cell (e.g. lymphocyte, monocyte, etc.) can be isolated through the use of antibodies against known cell surface markers that are specific for that cell type. Antibodies against cell surface markers of white blood cells are known to those of skill in the art. For instance, monoclonal antibodies specific for cell surface markers CD3, CD4, CD8, and CD19 are commercially available and can be used to select lymphocytes. Analysis for complement activation products found on the surface of white blood cells, such as BC4d, can be performed in an isolated fraction of white blood cells. The platelet fraction can be from other blood components to allow analysis of platelet-bound complement activation products, such as PC4d. Platelet isolation can be performed with methods known in the art, including differential centrifugation or immunoprecipitation using antibodies specific for platelets (e.g., CD42b).

The level (e.g., quantity or amount) of a particular biomarker can be measured in the sample using a variety of methods known to those of skill in the art. Such methods include, but are not limited to, flow cytometry, ELISA using red blood cell, platelet, or white blood cell lysates (e.g., lymphocyte lysates), and radioimmunoassay. In one embodiment, the determination of the level of C4d is made using flow cytometric methods, with measurements taken by direct or indirect immunofluorescence using polyclonal or monoclonal antibodies specific for each of the molecules. Each of these molecules can be measured with a separate sample (e.g., red blood cell-, white blood cell-, or platelet-specific fractions) or using a single sample (e.g., whole blood).

As used herein, "transformation analyses" can be any suitable mathematical operation, including but not limited to generalized models (e.g. logistic regression, generalized additive models), multivariate analysis (e.g. discriminant analysis, principal components analysis, factor analysis), and time-to-event "survival" analysis.

As will be understood by those of skill in the art based on the teachings herein, weighting coefficients can be determined by a variety of techniques and can vary widely. In one example of determining appropriate weighting coefficients, multivariable logistic regression (MLR) is performed using the maker levels found within two groups of patients, for example, one with and one without SLE. There are several methods for variable (marker) selection that can be used with MLR, whereby the markers not selected are eliminated from the model and the weighting coefficients for each predictive marker remaining in the model are determined. These weighting coefficients can then be, for example, multiplied by the marker level in the sample (expressed in any suitable units, including but not limited weight/volume, weight/weight, weight/number packed cells, etc.) and then, for example, summed to calculate an SLE risk score.

In one non-limiting embodiment, some components constituting the index score (for example, ANA and rule out markers) may be associated with predetermined threshold/cutoff values (for example, an ANA component might have a value of 0, 1 or 2; a rule out marker might have a value of 0 or 1). In such a scenario, the index can potentially change from positive to negative (or vice versa) based on the analytical error at the threshold decision limit for ANA or the rule-out markers. Thus, in some embodiments, "equivocal results" for the Index can be defined when components use to determine the index score are assessed using a threshold/cutoff value (for example, ANA and/or the rule out markers) and are within 20% or less of the threshold value (and therefore potentially able to affect the positivity or negativity of the index). In this embodiment, the score may be noted as equivocal.

As used herein, "combining" includes any mathematical operation to use markers in combination to arrive at a single score that can be compared to a threshold (adding, subtracting, dividing, multiplying, and combinations thereof). In these methods, the level of the markers may be adjusted using an appropriate weighting coefficient.

The methods may employ comparisons between a measured SLE risk score and a standard SLE risk score. Any suitable standard for comparison can be used, including but not limited to a pre-determined level or range of SLE risk scores from a normal individual or population of subjects suffering from SLE, or as otherwise described herein. As used herein, a "pre-determined level" or "pre-determined range" refers to a value or range of values that can be determined from the quantity or amount (e.g., absolute value or concentration) of a particular SLE risk score measured in a population of control subjects (i.e. healthy subjects) or a population of subjects afflicted with an autoimmune disease such as SLE, or a non-SLE autoimmune disorder. A pre-determined level or pre-determined range of SLE risk scores can be selected by calculating the value or range of SLE risk score values that achieves the greatest statistical significance. In some embodiments, the pre-determined level can be based on the variance of SLE risk scores from a population of control/normal subjects. For instance, the pre-determined level can be at least 2, 3, 4, or 5 standard deviations above the normal range SLE risk scores. A pre-determined level or pre-determined range SLE risk scores can also be determined by calculating a level or range of SLE risk scores for which greater than 50%, 60%, 70%, 75%, 80%, 85%, 90%, or 95% of patients having an SLE risk score within that level or range have SLE.

"Diagnosing/diagnosis," as used herein, means identifying the presence or nature of SLE. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Treating" the subject for SLE or another disease based at least in part on the SLE risk score means that those subjects identified as likely to have SLE based on their risk score are then treated for SLE as deemed appropriate by an attending physician or other medical professional. Such treatments may include, but are not limited to, immunosuppressants (ex: cyclophosphamide, corticosteroids, etc.) and/or disease modifying antirheumatic drugs (DMARDs; ex: methotrexate, azathiopurine, leflunomide, Belimumab, and antimalarials such as plaquenil and hydroxychloroquine). Disease-modifying antirheumatic drugs (DMARDs) are used preventively to reduce the incidence of flares, the process of the disease, and lower the need for steroid use; when flares occur, they are treated with corticosteroids.

The methods of all aspects of the invention as described herein can be carried out manually or may be used in conjunction with an automated system or computer. For instance, the methods can be performed using an automated system, in which a subject's blood sample is analyzed to make the determination or determinations of levels of particular biomarkers, and the comparison with the pre-determined level or pre-determined range is carried out automatically by software appropriate for that purpose. Computer software, or computer-readable media for use in the methods of this invention include: a computer readable medium comprising: (a) code for receiving data corresponding to a determination of complement component C4d deposited on surfaces of red blood cells, or lymphocytes (e.g., B cells), and for data corresponding to an amount of ANA, SS-B (La) marker, Scl-70 marker, Jo-1 marker, CENP marker, and/or anti-dsDNA antibodies is such samples in the biological sample; (b) code for retrieving a pre-determined level for complement component C4d deposited on surfaces of such cells of individuals, and for retrieving a predetermined level of ANA, SS-B (La) marker, Scl-70 marker, Jo-1 marker, CENP marker, and/or anti-dsDNA antibodies is such samples; and (c) code for comparing the data in (a) with the pre-determined level of (b) to make a determination whether an accurate SLE diagnosis can be made or whether additional measurements of other biomarkers are required In certain embodiments of the invention, one or more pre-determined levels or pre-determined ranges of biomarker levels may be stored in a memory associated with a digital computer. After data corresponding to a determination of complement C4d, ANA, SS-B (La) marker, Scl-70 marker, Jo-1 marker, CENP marker, and/or anti-dsDNA antibodies is such samples is obtained (e.g., from an appropriate analytical instrument), the digital computer can compare the measured biomarker data with one or more appropriate pre-determined levels or pre-determined ranges. After the comparisons take place, the digital computer can automatically calculate if the data is indicative of SLE diagnosis.

Accordingly, some embodiments of the invention may be embodied by computer code that is executed by a digital computer. The digital computer may be a micro, mini or large frame computer using any standard or specialized operating system such as a Windows based operating system. The code may be stored on any suitable computer readable media. Examples of computer readable media include magnetic, electronic, or optical disks, tapes, sticks, chips, etc. The code may also be written by those of ordinary skill in the art and in any suitable computer programming language including, C, C++, etc.

Thus, the invention further comprises non-transitory computer readable storage medium comprising a set of instructions for causing a device for measuring marker levels in a sample to carry out the method of any aspect or embodiment of the invention, In a further aspect, the present invention provides non-transitory computer readable storage media, for automatically carrying out the methods of the invention on a computer linked to a device for measuring levels of the recited markers in a sample, such as a blood sample. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system. Any suitable device for measuring marker levels can be used, including but not limited to flow cytometry devices and devices for carrying our ELISAs.

The present invention also provides kits and combinations of tests for diagnosing SLE. In one embodiment, the present invention includes a combination of tests useful for diagnosing SLE comprising at least three of (i.e. 3, 4, or all 5): a first test for the level of EC4d, a second test for the level of BC4d, a third test for the level of one or more (1, 2, 3, or all 4) of SS-B (La) marker, Scl-70 marker, Jo-1 marker, and a CENP marker, a fourth test for the level of ANA, and a fifth test for the level of anti-dsDNA antibodies. The kits or tests for determining the level of particular biomarkers include the various reagents for performing the measurements according to the methods described herein. For instance, in one embodiment, the kits or tests include reagents for performing immunofluorescence assays for each of the biomarkers, such as a conjugate of a monoclonal antibody specific for one or more markers specific for the recited targets with a fluorescent moiety. Additionally, the kits can comprise such other material as may be needed in carrying out assays of this type, for example, buffers, radiolabelled antibodies, colorimeter reagents, instructions for separating different cell fractions from whole blood, and instructions for diagnosing SLE based on particular pre-determined levels of the biomarkers.

In another embodiment, the kits or tests include reagents for performing other standard assays for each of the biomarkers, such as ELISA or radioimmunoassays. In such embodiments, the kits or tests comprise monoclonal antibodies or other markers specific for the recited targets conjugated with appropriate labels such as radioactive iodine, avidin, biotin or enzymes such as peroxidase. The kits can additionally comprise buffers, substrates for antibody-conjugated enzymes, instructions for separating different cell fractions from whole blood, and instructions for diagnosing SLE based on particular pre-determined levels of the biomarkers.

It is understood that the examples and embodiments described herein are for illustrative purposes only and that various modifications or changes in light thereof will be suggested to persons skilled in the art and are to be included within the spirit and purview of this application and scope of the appended claims. All references, publications, patents, and patent applications cited herein are hereby incorporated by reference in their entireties for all purposes.

EXAMPLE

Introduction

Systemic lupus erythematosus (SLE) is a chronic autoimmune disease resulting in autoantibody-mediated tissue damages and potentially life-threatening multi-organ failure (1). This heterogeneous inflammatory disease affects from 161,000 to 322,000 adults in the United States with females being affected 9 times more often than men (2). In addition, the prevalence rate is higher in African Americans and Hispanics compared to Caucasians and socio-demographic background is predictive of poor prognosis (3). The manifestations of SLE are diverse and include rash, arthritis, anemia, thrombocytopenia, serositis, nephritis, seizures, and psychosis. Because these symptoms are heterogeneous, non-specific, evolutive, and often mimic those of other diseases, the diagnosis of SLE is complex and can be challenging to physicians. Diagnosing SLE relies on a combination of the patient's medical history, current symptoms, and laboratory tests. Although the revised American College of Rheumatology criteria published in 1982 (4) requires the presence of 4 of 11 criteria to classify a patient as having SLE, the use of these criteria in clinical practice is not uniform (5). Among the standard laboratory tests commonly used to support the diagnosis of SLE are primarily antinuclear antibodies (ANA) and anti-double stranded DNA (anti-dsDNA) antibodies (6). Nonetheless, ANA and anti-dsDNA antibodies have limitations and neither of these serological markers provides adequate balanced sensitivity and/or specificity to diagnose SLE. It is well recognized that complement activation is central to the pathogenesis of SLE (7), and cell bound C4d fragment deposited on erythrocytes and B lymphocytes can facilitate the diagnosis of SLE (8-11). In addition, reports have established the potential contribution of CB-CAPs to disease activity (12;13) and their measurement may help treating physicians with the management of SLE patients.

We previously established the contribution of CB-CAPs to SLE diagnosis in a large multi-centered cross-sectional study (14) and our data confirmed that excessive C4d complement deposition on erythrocytes, B cells, platelets and alternatively lower CR1 expression on erythrocytes were generally several-fold different in SLE compared to other diseases (14). However, significant overlap in the expression of these markers was observed between SLE and other rheumatic diseases, thereby indicating that none of the individual CB-CAPs achieved adequate balanced clinical sensitivity and specificity alone (15). In this study anti-dsDNA was an insensitive (29.5%) yet specific marker (>95%), whereas ANA was a sensitive but poorly specific marker. We relied on the high anti-dsDNA antibody specificity (low false positive rate) to evaluate the incremental diagnostic value of CB-CAPs ANA and anti-MCV. Among anti-dsDNA negative individuals, the stepwise addition of log normalized EC4d and BC4d markers significantly increased sensitivity while maintaining adequate specificity. The specificity gain further contributed by anti-MCV was dependent on rheumatoid arthritis (RA) (specificity against RA was 87.7% without vs. 97.4% with anti-MCV) and enabled the selection of a more optimal cutoff increasing overall SLE sensitivity. The index score (>0) combining the weighed sum of ANA, EC4d, BC4d together with anti-MCV was sensitive (71.6%) and specific (90.1%) for SLE. Altogether, the combination of anti-DNA and the index score improved the clinical sensitivity vs. anti-DNA alone from 29.5% to 80.0%. This 50.5% improvement in clinical sensitivity largely outweighed the 9.6% loss in specificity from 96.1% to 86.5%. Moreover, when compared to anti-dsDNA and ANA combined, anti-dsDNA with the index resulted into a 30.3% improvement in specificity (59.0% vs. 89.3%) with only a 10.0% loss in sensitivity (89.0% vs. 79.0%).

However, while the specificity of our diagnostic method was high against patients with RA, the specificity against other diseases including scleroderma dermatomyositis, vasculitis and Sjogren's Syndrome was significantly lower than 75% and therefore potentially limited the value of our diagnostic method in clinical practice Methods Clinical Protocol and Validation Plan The performances characteristics of the multivariate index were established in two cohorts of subjects enrolled from May to August 2010 (cohort 1) and from June 2011 to September 2013) (Cohort 2).

Study Design and Plan

The two independent studies (cohort 1 and 2) were multi-centered, cross-sectional studies and required one subject visit. There were no follow-up visits required to evaluate the performance characteristics of the diagnostic methodology. After the subject's informed consent was obtained, the following procedures were performed:

The subject's medical history related to the diagnosis of any and all rheumatologic conditions was obtained and reviewed for inclusion/exclusion criteria and details regarding the diagnosis of these conditions;

The date of diagnosis was recorded for SLE and other rheumatologic conditions, and the specific SLE diagnostic criteria met was documented (revised ACR Criteria for the Classification of SLE) (Tan et al., 1982; Hochberg, 1997);

Subject demographics were documented (date of birth, gender, race/ethnicity).

A urine pregnancy test via dipstick was performed on all females of child-bearing potential;

Approximately 15 mL of patient's blood was obtained for analysis of CB-CAPS (EC4d and BC4d), ANA, anti-dsDNA, anti-MCV and ENA antibodies; the blood sample was obtained under either fasting or non-fasting conditions. The sample consisted of one 7.5-ml EDTA tube (lavender top), and one SST tube (red tiger top), which required centrifugation prior to shipping. All biological samples were sent by overnight delivery from the study site to Exagen Diagnostics (using transportation kits provided). Because CB-CAPS should be analyzed within 48 hours of sample collection (see pre-analytical variables project ID 25945), samples were not accepted on Saturday; therefore, subjects were only enrolled from Monday through Thursday (Thursday shipping cut-off time was 10:00 a.m.).

The blood was obtained and shipped by the site to Exagen Diagnostics (San Diego based facility). In order to preserve blinding in the analytical laboratory, CRFs and any subject information that would disclose the subject's diagnosis were faxed to the Exagen clinical project manager, whereas blood samples for analysis were sent directly to the analytical laboratory, accompanied by a completed subject-specific requisition form. Results of these tests were not made available to the investigator during the conduct of the study. Specimens were identified only by subject number and initials and the analytical lab remained blinded to subject-specific diagnosis. Only the clinical team had access to patients' diagnoses throughout the study.

Erythrocytes and B-lymphocytes were isolated, washed, immunofluorescently labeled using monoclonal and/or polyclonal antibodies specific for C4d, and analyzed by flow cytometry using the assay validated in our clinical laboratory. Mean fluorescence intensity was used as an indicator of expression level of each cell surface marker; dsDNA, ANA, anti-MCV and antibodies to ENA were measured using solid phase immunoassays cleared by the FDA as in-vitro diagnostics. Manufacturer cutoffs were used for all ELISA expect for anti-MCV.

Selection of Study Population

Inclusion Criteria:

Able to read, understand, and sign the informed consent form

≥18 years of age

Agree to and able to have blood sample collected

Subjects with rheumatologic conditions must fall into one of the following two categories:

Diagnosed with SLE according to the revised ACR Criteria for the Classification of SLE.

Table 1 illustrates the Criteria for the Classification of SLE.

TABLE 1

ACR criteria for SLE

Criteria

Malar rash: Fixed erythema, flat or raised, over the malar eminences
Discoid rash: Erythematous circular raised patches with adherent keratotic scaling and follicular plugging; atrophic scarring may occur
Photosensitivity: Exposure to ultraviolet light causes rash
Oral ulcers: Includes oral and nasopharyngeal ulcers, observed by physician
Arthritis: Nonerosive arthritis of two or more peripheral joints, with tenderness, swelling, or effusion
Serositis: Pleuritis or pericarditis documented by ECG or rub or evidence of effusion
Renal disorder: Proteinuria >0.5 g/d or 3+, or cellular casts
Neurologic disorder: Seizures or psychosis without other causes
Hematologic disorder: Hemolytic anemia or leukopenia (<4000/L) or lymphopenia (<1500/L) or thrombocytopenia (<100,000/L) in the absence of offending drugs
Immunologic disorder: Anti-dsDNA, anti-Sm, and/or anti-phospholipid
Antinuclear antibodies: An abnormal titer of ANA by immunofluorescence or an equivalent assay at any point in time in the absence of drugs known to induce ANAs Any combination of 4 or more of 11 criteria, well-documented at any time during a patient's history, makes it likely that the patient has SLE.

Diagnosed with one of the following rheumatologic disorders: Anti-Phospholipid Syndrome (APS); fibromyalgia (ANA+ patients only); systemic sclerosis; rheumatoid arthritis, polymyositis; dermatomyositis; Wegeners granulomatosus; polyarteritis nodosa; cryoglobulinemic vasculitis; leukocytoclastic vasculitis; other immunologic vasculitides; primary Sjogren's Syndrome.

In addition, approximately 200 normal healthy volunteers (Refer to Exclusion Criteria) were enrolled.

Exclusion Criteria:

For normal healthy volunteers only: Based on the Principal Investigator's judgment, clinically significant, concurrent morbidity including cardiovascular, psychiatric, neurologic, gastrointestinal (e.g., gastric or duodenal ulcers, inflammatory bowel disease, history of GI bleeds), metabolic, pulmonary (e.g., asthma, COPD), renal (including renal insufficiency), hepatic, hematologic, immunologic, endocrine (e.g., hypothyroidism, diabetes), active infection or history of chronic infectious disease (Hepatitis B or C or HIV), neoplastic disease, and/or history of weight loss surgery.

Overt or laboratory evidence of primary immunodeficiency syndromes

Pregnant or lactating women.

Trial Procedure

Data on a total of 800 subjects consisting of approximately 300 SLE, 300 non-SLE rheumatologic diseases, and 200 healthy controls gathered from approximately 15 participating centers in the United States were planned for the two cohorts of subjects. Participating centers were encouraged to recruit an equivalent number of subjects with SLE and other rheumatologic conditions to ensure a balanced sample. Blood was drawn from each subject for CB-CAPS and other serological markers.

All data and blood samples submitted to the Sponsor were kept strictly anonymous by the use of subject I.D. numbers. Each center was assigned a two digit site number, and each center assigned a secondary I.D. number. Each center was responsible for maintaining a list of study numbers and associated subject names at their site. All subject identifiers were removed from any supporting documentation and all blood samples were identified only by subject I.D. numbers and initials. In addition, the Sponsor's clinical laboratory was blinded to all subjects' diagnoses.

Statistical Analysis

Statistical analysis was conducted using the R software version 2.15.0. Statistical analyses utilized area under receiver operating characteristic (ROC) curves (SLE vs. non-SLE patients excluding normal subjects), and calculations of diagnostic sensitivity and specificity. Receiver operating curves were used as appropriate for each of the markers (univariate analysis) and also following the determination of an index value as the output of multivariate logistic regression equation. As measures of performance, sensitivity and specificity were computed. The reported performance statistics (sensitivity, specificity), ROC AUC were calculated using leave-one-out cross validation.

Clinical Performances

A total of 304 SLE patients, 285 patients with other rheumatic diseases (87.8% females, mean age 48 y) were eligible for the analysis. The group of 285 patients with other rheumatic diseases included RA (161 patients, 85% females, mean age 59 years), systemic sclerosis (35 patients, 80% females, mean age 53 years) polymyositis/dermatomyositis (PM/DM: 27 patients, 81% females, mean age 56 years), primary Sjogren's Syndrome (33 patients, 94% females, mean age 56 years), and 29 patients with various other rheumatic diseases (83% females, mean age 55 years) (Granulomatosis with Polyangiitis [5 patients], fibromyalgia [13 patients], vasculitis [10 patients], antiphospholipid syndrome [1 patient]). Also a total of 205 healthy individuals (66% females, mean age 41 y) were enrolled. (Table 2).

TABLE 2

Distribution of patients in the two cohorts

| | Cohort 1 | Cohort 2 | Total |
|---|---|---|---|
| SLE | 210 | 94 | 304 |
| RA | 120 | 41 | 161 |
| Sjogren's | 9 | 24 | 33 |
| Scleroderma | 21 | 14 | 35 |
| PM/DM | 16 | 11 | 27 |
| Other dis. | 12 | 17 | 29 |
| NHV | 205 | 0 | 205 |
| TOTAL | 593 | 201 | 794 |

The characteristics of 304 patients are presented in Table 3.

TABLE 3

Characteristics of the 304 SLE patients enrolled

| | N (%) |
|---|---|
| Gender (female) | 277 (91%) |
| Race | |
| Caucasians | 124 (41%) |
| African Americans | 92 (30%) |
| Asians | 22 (7%) |
| Hispanics | 61 (20%) |
| Others | 5 (2%) |
| Malar rash | 141 (46%) |
| Discoid rash | 44 (14%) |
| Photosensitivity | 118 (39%) |
| Oral ulcers | 97 (32%) |
| Arthritis | 232 (76%) |
| Serositis: | 91 (30%) |
| Pleuritis | 63 (21%) |
| Pericarditis | 41 (13%) |
| Renal Disorder: | 133 (44%) |
| Proteinuria >0.5 g/d | 123 (40%) |
| 3+ cellular casts | 15 (5%) |
| Neurological disorder: | 22 (7%) |
| Seizures | 20 (7%) |
| Psychosis w/o other causes | 4 (1%) |
| Hematologic disorder: | 161 (53%) |
| Hemolytic anemia | 16 (5%) |
| Leukopenia (<4000/L) | 79 (26%) |

TABLE 3-continued

Characteristics of the 304 SLE patients enrolled

| | N (%) |
|---|---|
| Lymphopenia (<1500/L) | 84 (28%) |
| Thrombocytopenia (<100,000/L) | 40 (13%) |
| Immunologic disorder: | 249 (82%) |
| anti-dsDNA | 206 (68%) |
| anti-Sm | 71 (23%) |
| anti-phospholipid | 76 (25%) |
| Antinuclear antibodies | 293 (96%) |

Univariate Analysis of Markers Used in SLE Diagnostic Method

Serological markers (ANA, anti-dsDNA, anti-MCV, SS-B/La, CENP, Scl-70, Smith) and CB-CAPs were determined in all subjects enrolled (n=794). ANA (≥20 units) was sensitive marker (91.7%, 279 SLE patients tested positives) yet largely non-specific against other rheumatic diseases (52.3%) (Table 4).

Among the 304 patients with SLE, a total of 101 SLE of them tested positive for anti-dsDNA by solid phase assay (33.2%), and 97 test results were confirmed positive using a Crithidia Luciliae indirect immunoflurorescence assay (INOVO Diagnositcs), thus yielding a final sensitivity of 31.9% (97/304). A total of 11 non-SLE subjects (6 RA, 2 scleroderma, 2 vasculitis and 1 normal) tested positive for antidsDNA by ELISA (>301 units), but 3 of them (2 RA and 1 scleroderma) were not confirmed positive by the Crithidia assay, thus yielding a specificity of 97.2% (277/285) against other diseases and 99.5% against normal healthy individuals (204/205). Anti-Smith was a poorly sensitive (14%) but highly specific marker for SLE (100%). Alternatively, anti-MCV (cutoff 70 units), SS-B/La (>10 units), SCl-70 (>10 units) and Jo-1 (>10 units) were specific for rheumatoid arthritis, Sjogren's, scleroderma and PM/DM patients, respectively (Table 4).

TABLE 4

Marker performances by univariate analysis

| | SLE | RA | Sjogren's | Scl* | PM/DM | Others | NHV |
|---|---|---|---|---|---|---|---|
| ANA ≥20 Units | 91.7% | 3% | 88% | 66% | 7% | 31% | 9% |
| | (279) | (51) | (29) | (23) | (24) | (9) | (19) |
| dsDNA >301 Units confirmed Crithidia | 32% | 2% | 0% | 3% | 0% | 7% | 0% |
| | (97) | (4) | (0) | (1) | (0) | (2) | (1) |
| AntiSm >10 Units | 14% | 0% | 0% | 0% | 0% | 0% | 0% |
| | (42) | (0) | (0) | (0) | (0) | (0) | (0) |
| AntiMCV >70 Units | 3% | 47% | 9% | 6% | 4% | 3% | 0% |
| | (8) | (76) | (3) | (2) | (1) | (1) | (1) |
| Jo1 >10 Units | 0% | 0% | 0% | 0% | 15% | 0% | 0% |
| | (0) | (0) | (0) | (0) | (4) | (0) | (0) |
| Scl-70 >10 Units | 0% | 0% | 3% | 20% | 0% | 0% | 0% |
| | (0) | (0) | (1) | (7) | (0) | (0) | (0) |
| SS-B/La >10 Units | 9% | 1% | 39% | 3% | 0% | 0% | 0% |
| | (27) | (1) | (13) | (1) | (0) | (0) | (0) |
| CENP >10 Units | 2% | 3% | 3% | 17% | 0% | 0% | 1% |
| | (6) | (5) | (1) | (6) | (0) | (0) | (2) |

*Scl: Scleroderma

As presented in Table 5 EC4d and BC4d levels were several-fold higher in SLE than other diseases or normal subjects. EC4d levels above 75 units or BC4d levels above 200 units were highly specific for SLE. Only 2/285 subjects with other diseases (one RA and one vasculitis) presented with EC4d or BC4d levels above 75 and 200 units, respectively (specificity 99.3%). Alternatively, a total of 48 SLE patients (16% presented with elevated EC4d or BC4d).

Also, EC4d levels above 12 MFI were 97% specific in distinguishing NHV from SLE while BC4d levels above 48 units were 96% specific.

TABLE 5

EC4d and BC4d levels

| | SLE | RA | Sjogren's | Scl* | PM/DM | Others | NHV |
|---|---|---|---|---|---|---|---|
| EC4d Net MFI | 21 ± 3 | 8 ± 1 | 10 ± 2 | 7 ± 1 | 8 ± 1 | 7 ± 1 | 5 ± 1 |
| EC4d>12 Units | 54.6% | 10.6% | 21.2% | 11.4% | 14.8% | 17.2% | 2.4% |
| EC4d>75 Units | 2.3% | 0.6% | 0.0% | 0.0% | 0.0% | 0.0% | 0.0% |
| BC4d Net MFI | 106 ± 6 | 32 ± 2 | 26 ± 4 | 32 ± 5 | 27 ± 4 | 46 ± 19 | 23 ± 3 |
| BC4d>48 Units | 62.2% | 14.3% | 12.1% | 17.1% | 3.7% | 10.3% | 4.4% |
| BC4d>200 Units | 14.1% | 0.0% | 0.0% | 0.0% | 0.0% | 3.4% | 0.0% |

*Scl: Scleroderma;

Results are expressed as mean ± standard error of the mean

Multivariate Index Assay—Post Analytical Reduction of the Data

The diagnostic methodology used employs a two-tier approach. In Tier 1, positivity for anti-dsDNA (>301 units; confirmed by Crithidia), or anti-Smith (>10 units; manufacturer cutoff, a criteria for SLE), or high EC4d (>75 units), or BC4d (>200 units) is suggestive of SLE. In Tier-2 determined among subjects negative in tier 1, a weighted index score cumulates an ANA component (ANA≥20 units, ≥60 units), a CBCAPS component (log normalized EC4d plus BC4d) and a specificity component consisting of positivity for anti-MCV (>70 units; RA marker), or SS-/La (>10 units; Sjogren's disease marker), or CENP/Scl-70 (>10 units, scleroderma marker), or Jo-1 (>10 units; polymyositis/dermatomyositis). An index>0 is suggestive of SLE, and the two-tier combination results in the overall performance characteristics. FIG. 1 summarizes the two-tiered diagnostic methodology employed.

Tier1: Performance Characteristics:

Among 794 subjects enrolled, a total of 150 of them tested positive for at least one of the tier 1 markers (dsDNA>301 units confirmed by Crithidia, or anti-Sm>10 units, or EC4d>75 units, or BC4d>200 units). Of these 150 subjects, 140 of them had SLE (sensitivity 46.1%, 140/304) while 9 of them has other rheumatic diseases (5 RA, 1 systemic sclerosis, 2 vasculitis, 1 APS, along with 1 normal) (specificity of 96.8%, 276/285). Specificity in distinguishing normal healthy subjects was 99.5% (204/205) (Table 6).

TABLE 6

Positivity in Tier 1

| | Positive Tier 1 | Percent |
|---|---|---|
| SLE | 140/304 | 46.1% |
| RA | 5/161 | 3.1% |
| Sjogren's | 0/33 | 0.0% |
| Scleroderma | 1/35 | 2.9% |
| PM/DM | 0/27 | 0.0% |
| Other dis. | 3/29 | 10.3% |
| NHV | 1/205 | 0.5% |

Among the 140 SLE patients positive in Tier 1 a total of 48 of them (34.3%) tested positive for EC4d>75 units or BC4d>200 units. It follows that a total of 645 subjects (165 SLE, 276 other diseases and 204 normal healthy tested negative in tier-1, were analyzed in tier 2 by logistic regression.

Tier 2 Performances Characteristics

Logistic regression analysis among patients with SLE (n=165) and other diseases (n=111) utilized positivity for ANA by ELISA (ANA component) together with the log normalized EC4d and BC4d levels (CBCAPS component) and an antibody specificity component composite of positivity for antiMCV (>70 units), SS-B/La (>10 units), CENP (>10 units), Scl-70 (>10 units) or Jo-1 (>10 units).

The ANA component of the multivariate logistic regression utilized two thresholds. This consisted of negative ANA (ANA<20 units; in that case the ANA component was affected with a value of 0), moderate positive (ANA 20-60 units; in that case the ANA component was affected with a value of 1) and strong positive (>60 units; ANA. in that case the ANA component was affected with a value of 2). Positivity for the antibody specificity component was 9.1% in SLE (15/164 positives) compared to 40.2% in subjects with other diseases (111/276 subjects). Only 3 normal subjects were positive for the specificity component in Tier 2.

TABLE 7

Positivity for Specificity component among subjects in Tier-2

| | Positive Tier 1 | Percent |
|---|---|---|
| SLE | 15/164 | 9.1% |
| RA | 74/156 | 47.4% |
| Sjogren's | 17/33 | 51.5% |
| Scleroderma | 15/34 | 44.1% |
| PM/DM | 4/27 | 14.8% |
| Other dis. | 1/26 | 3.8% |
| NHV | 3/204 | 1.5% |

Table 8 highlights the estimates of multivariate logistic regression in Tier2. Estimates were calculated using SLE and non SLE subjects excluding normal healthy individuals.

TABLE 8

Logistic regression estimates

| | Estimate | P value |
|---|---|---|
| (Intercept) | −5.2626 ± 0.6790 | <0.001 |
| ANA component | 0.9877 ± 0.1585 | <0.001 |
| LOG(EC4d) | 0.2955 ± 0.2040 | 0.148 |
| LOG(BC4d) | 1.0260 ± 0.1936 | <0.001 |
| Specificity component | −2.4944 ± 0.3507 | <0.001 |

The Index Equation, in Tier 1 negative patients, corresponding to the output of the logistic regression model follows:

$$\text{Index} = -5.2626 + 0.9877 \times ANAComp + [0.2955 \times \log(EC4d) + 1.0260 \times \log(BC4d)] - 2.4944 \times SpecComp$$

ANA component: If ANA<20 units; ANA component was affected with a value of 0); If ANA was moderate positive (ANA 20-60 units, the ANA component was affected with a value of 1). If ANA was strong positive (≥60 units), the ANA component was affected with a value of 2; Specificity component (Spec.Comp): if all markers part of the specificity component (anti-MCV>70 units; SS-B/La>10 units; CENP>10 units; Scl-70>10 units, or Jo-1>10 units) were below their respective cutoff value, the result was entered as 0; Conversely, if any of the markers of the specificity component were above their respective cutoff the result was entered as 1. Log corresponds to the natural log of net MFI for EC4d and BC4d.

An example of index calculation is provided in Table 9.

TABLE 9

Index Calculation

| Analyte | Results | Component index | Index Calculation | Interpretation |
|---|---|---|---|---|
| ANA component CBCAPS component | ANA: 35 Units EC4d = 15 units BC4d = 60 units | ANA component = 1 logEC4d = 2.708; log BC4d = 4.094 CBCAPS component: 0.2955 × 2.708 + 1.0265 × 4.094 = 5.001 | =−5.2626 + 0.9877 × 1 + 5.001 − 2.4944 × 1 = −1.77 | Index < 0; Non Suggestive of SLE |
| Specificity component | SSB-La: 2 units (0) CENP: 20 units (1) AntiMCV: 150 units (1) Jo-1: 0 units (0) Scl-70 2 units (0) | 0 + 1 + 1 + 0 + 0 = 0 > 0 Specificity var = 1 | | |

TABLE 10

Index values in Tier 2

| | N | 25% perc. | median | 75% perc. | Index > 0 |
|---|---|---|---|---|---|
| SLE | 165 | −0.64 | 0.47 | 1.79 | 63.6% (105/165) |
| RA | 156 | −3.25 | −2.17 | −1.09 | 5.1% (8/156) |
| Sjogren's | 33 | −2.12 | −1.31 | 0.13 | 30.3% (10/33) |
| Scleroderma | 34 | −1.94 | −1.62 | −1.13 | 5.9% (2/34) |
| PM/DM | 27 | −1.78 | −1.14 | 0.07 | 25.9% (7/27) |
| Other dis. | 26 | −2.08 | −1.62 | −1.16 | 15.4% (4/26) |
| NHV | 204 | −2.07 | −1.67 | −1.38 | 2.5% (5/204) |

Figure 2:
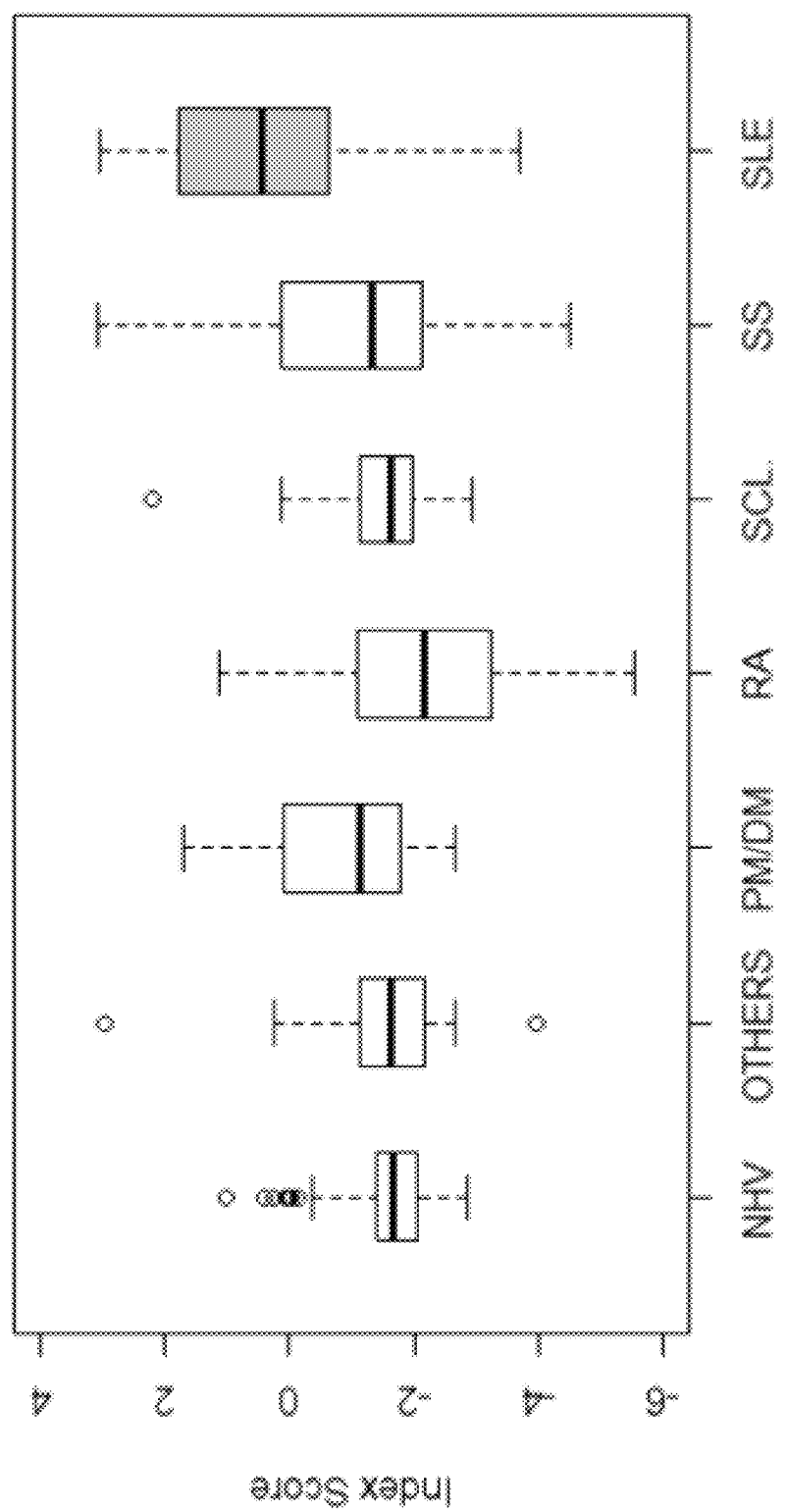
FIG. 2 is a graph showing index score among anti-dsDNA negative subjects. RA: rheumatoid arthritis; PM/DM: polymyositis/dermatomyositis; Scl.: sclerderma; SS: Sjogren's syndrome; NHV: normal healthy volunteers.

The Index score was −1.74 (median) (IQ range: −2.54; −0.90) in other diseases, and 0.47 (median) (IQ range: −0.64; 1.79) in SLE (FIG. 2). It was −1.46 (median) (IQ range: −1.17; −1.86) in NHV, Table 10 highlights the median index values observed in SLE and the control group (non-SLE and NHV). Sensitivity was 63.6%, specificity against other diseases was 88.8% (245/276) patients and 97.5% against normal healthy subjects (199/204). A cutoff set at −2.5 units resulted in 98.7% sensitivity for SLE and 24.9% specificity for other rheumatic diseases (5.8% specificity for normal healthy). Alternatively, a cutoff set +2.5 units results in 50.0% sensitivity for SLE and 96.1% specificity for other rheumatic diseases (100% specificity for normal healthy).

Overall Performances Characteristics—Two Tiered Combined

A combination of Tier 1 and the Index score (using a cutoff of zero) yielded 80.3% (244/304) sensitivity for SLE, and 85.5% (236/276) specificity in distinguishing SLE from other rheumatic diseases. Specificity in distinguishing SLE from healthy subjects was 97.1% (199/205). The result of two-tier analysis combined is presented in Table 11.

TABLE 11

Overall performances two-tier method combined

| | Total # | Tier 1% (N) | Tier 2 # | Tier 2% (N) | Total pos. | Total % |
|---|---|---|---|---|---|---|
| SLE | 304 | 45.7% (139/304) | 165 | 63.6% (105/165) | 244 | 80.3% (244/304) |
| RA | 161 | 3.1% (5/161) | 156 | 5.1% (8/156) | 13 | 8.1% (13/161) |
| Sjogren's | 33 | 0.0% (0/33) | 33 | 30.3% (10/33) | 10 | 30.3% (10/33) |
| Scleroderma | 35 | 2.9% (1/35) | 34 | 5.9% (2/34) | 3 | 8.6% (3/35) |
| PM/DM | 27 | 0.0% (0/27) | 27 | 25.9% (7/27) | 7 | 25.9% (7/27) |
| Other dis. | 29 | 10.3% (3/29) | 26 | 15.4% (4/26) | 7 | 24.1% (7/29) |
| NHV | 205 | 0.5% (1/205) | 204 | 2.5% (5/204) | 6 | 2.9% (6/205) |

Stepwise Addition of CBCAPS and Specificity Components to Base Model

The performances characteristics of the two-tier methods were also compared to those obtained without the CBCAPs (EC4d and BC4d) and specificity components ("base model). The base model consisted of two-tier analysis with anti-dsDNA and anti-Sm in tier-1, and the ANA component in Tier-2. The stepwise addition of CBCAPS and specificity components is presented in Table 12. As presented in Table 13 the addition of CBCAPS and specificity components improved the performances characteristics and the base model, and yielded an AUC of 0.894, with sensitivity of 80% and 86% specificity in distinguishing SLE from other diseases. The antibody specificity component maximizes the specificity of the diagnostic methodology for RA, primary Sjogren's, PM/DM and systemic sclerosis. Specificity in distinguishing normal subjects from SLE was 90.2% for base model, 94.1% for the model with CBCAPS and 97.1% for the full model.

TABLE 12

Model comparison

| | Tier1 | Tier2 |
|---|---|---|
| Base Model | AntidsDNA > 301 U; AntiSm > 10 U | ANA component |
| Base Model + CBCAPS | AntidsDNA > 301 U; AntiSm > 10 U; EC4d > 75 U; BC4d > 200 U | ANA component CBCAPS component |
| Base Model + CBCAPS + Specificity component | AntidsDNA > 301 U; AntiSm > 10 U; EC4d > 75 U; BC4d > 200 U | ANA component CBCAPS component Antibody Specificity component |

TABLE 13

Stepwise addition of CBCAPS and specificity component

| | N | Base Model ANA, dsDNA, AntiSm | Base Model + CBCAPS | Base Model + CBCAPS + Spec. comp. | Difference from base model |
|---|---|---|---|---|---|
| Spec. primary Sjogren's | 33 | 12% | 52% | 70% | 57.6% |
| Spec. systemic sclerosis | 35 | 34% | 57% | 91% | 57.1% |
| Spec. PM/DM | 27 | 26% | 59% | 74% | 48.1% |
| Spec. rheumatoid arthritis | 161 | 68% | 78% | 92% | 23.6% |
| Spec. Other diseases | 29 | 69% | 76% | 76% | 6.9% |
| Total Specificity (non-SLE) | 285 | 54% | 70% | 86% | 32.3% |
| Total Sensitivity (SLE) | 304 | 89% | 84% | 80% | −8.6% |
| AUC | 589 | 0.718 | 0.859 | 0.894 | 0.176 |

Cohort Analysis and Comparison with Previous Methods

The difference in sensitivity between the two cohorts (cohort 1=81% vs cohort 2=79%) was not statistically significant (p=0.652) (overall sensitivity=80%). Also, the difference in specificity in distinguishing SLE from other diseases was not statistically significant (cohort 1=87% vs. cohort 2=84%; p=0.485) (overall specificity=86%). We also compared the performance characteristics of the current two tiered method with those from current assays (Table 14). The addition of serological markers specific for connective tissues diseases (SS-B/La; Scl-70; CENP; Jo-1) improves the specificity of the diagnostic methodology from 64% to 79% (combined dataset: p=0.024).

TABLE 14

Performances characteristic comparison

| | | Cohort 1 | Cohort 2 | Combined |
|---|---|---|---|---|
| Previous | Sensitivity SLE: | 80% (169/210) | 82% (77/94) | 81% (246/304) |
| | Specificity Non-SLE: | 86% (153/178) | 74% (79/107) | 81% (232/285) |
| | RA: | 92% (110/120) | 93% (38/41) | 92% (148/161) |
| | Conn. Tissue: | 74% (34/46) | 55% (27/49) | 64% (61/95) |
| | Other diseases: | 75% (9/12) | 82% (14/17) | 79% (23/29) |
| Current 2 Tiered method | Sensitivity SLE: | 81% (170/210) | 79% (74/94) | 80% (244/304) |
| | Specificity Non-SLE: | 87% (155/178) | 84% (90/107) | 86% (245/285) |
| | RA: | 90% (108/120) | 98% (40/41) | 92% (148/161) |
| | Conn. Tissue: | 83% (38/46) | 76% (37/49) | 79% (75/95) |
| | Other diseases: | 75% (9/12) | 76% (13/17) | 76% (22/29) |

Analytical Reproducibility of the Index

The day to day reproducibility of the Index was also determined in a total of 19 samples from 11 patients with SLE. For patients having multiple index determination the blood was collected at one week interval. None of these patients were part of the clinical validation studies (cohort 1 and Cohort 2). The Index composite of ANA, CBCAPS and antibody specificity components was determined 3 consecutive times on 3 consecutive days. Table 15 highlights the between day variability.

TABLE 15

Analytical variability of the Index

| PN | visit | Day 1 | Day 2 | Day 3 | Day 4 | average | stdev |
|---|---|---|---|---|---|---|---|
| CL001-001-01 | 1 | −0.74 | −0.85 | −0.53 | −0.70 | −0.70 | 0.13 |
| CL001-001-02 | 2 | −0.82 | −0.65 | −0.62 | −0.77 | −0.72 | 0.10 |
| CL001-002-01 | 1 | 1.48 | 1.32 | 1.31 | 1.22 | 1.33 | 0.11 |
| CL001-002-02 | 2 | 0.89 | 1.25 | 0.92 | 0.73 | 0.95 | 0.22 |
| CL001-003-02 | 1 | 2.54 | 2.56 | 2.70 | 2.53 | 2.58 | 0.08 |
| CL001-004-01 | 1 | 0.90 | 1.28 | 1.33 | 0.82 | 1.08 | 0.26 |
| CL001-004-02 | 2 | 0.39 | 0.39 | 0.25 | 0.23 | 0.31 | 0.08 |
| CL001-004-03 | 3 | 0.31 | 0.34 | 0.26 | 0.04 | 0.24 | 0.14 |
| CL001-005-01 | 5 | 0.09 | 0.27 | 0.19 | 0.28 | 0.21 | 0.09 |
| CL001-005-03 | 2 | 0.42 | 0.25 | 0.44 | 0.32 | 0.36 | 0.09 |
| CL001-006-01 | 1 | 0.75 | 0.30 | 0.69 | 0.67 | 0.60 | 0.21 |
| CL001-006-03 | 2 | 0.78 | 0.86 | 0.73 | 0.35 | 0.68 | 0.23 |
| CL001-007-01 | 1 | 2.36 | 2.42 | 2.33 | 2.36 | 2.37 | 0.04 |
| CL001-008-01 | 1 | −1.12 | −1.10 | −1.18 | −1.23 | −1.16 | 0.06 |
| CL001-008-02 | 2 | −0.82 | −1.18 | −1.19 | −0.98 | −1.04 | 0.18 |
| CL001-009-02 | 1 | −1.56 | −1.48 | −1.46 | −1.68 | −1.54 | 0.10 |
| CL001-010-02 | 2 | −0.51 | −0.44 | −0.44 | −0.49 | −0.47 | 0.03 |
| CL001-011-01 | 1 | 2.96 | 2.74 | 2.91 | 2.95 | 2.89 | 0.10 |
| CL001-011-02 | 2 | 2.91 | 2.95 | 2.97 | 3.03 | 2.96 | 0.05 |
| CL001-001-01 | 1 | −0.74 | −0.85 | −0.53 | −0.70 | −0.70 | 0.13 |

Median standard deviation was 0.12 (range 0.03 to 0.26).

Definition of Equivocal Results

Equivocal Index Results Based on Equivocal ANA and Specificity Components

Because two of the three components constituting the index score (ANA and antibody specificity components) are associated with cutoff values (ANA component can have a value of 0, 1 or 2; antibody specificity component can have a value of 0 or 1), the index can potentially change from positive to negative (or vice versa) based on the analytical error at the medical decision limit for ANA (20 units; 60 units) or each of the marker forming the specificity component (anti-CV [70 units]; SS-B/La [10 units], CENP [10 units], Jo-1 [10 units] or Scl-70 [10 units]). For example, in as presented in Table 16 the index can change from −1.0 (case 2, SS-B/La=9 units; specificity component=0) to +1.5 (case 1, SS-B/La=1 units; specificity component=1) based on two units SS-B/La difference at the decision limit of 10 units (9 vs. 11 Units).

TABLE 16

Effect of marker levels on Index Score

| | ANA | Spec. component | CBCAPS component | INDEX |
|---|---|---|---|---|
| Case 1 | ANA = 100 units<br>ANA component = 2 | MCV = 5 units SS-B = 9 units CENP = 1 unit;<br>SCL-70 = 2 units;<br>Jo-1 = 0 units<br>Spec. component = 0 | EC4d = 15 units<br>BC4d = 50 units<br>CBCAPS comp. = 4.814 | =−5.2626 + 0.9877 × 2 + 4.814 + −2.4944 × 0 = +1.5<br>SUGGESTIVE |
| Case 2 | ANA = 100 units<br>ANA component = 2 | MCV = 5 units SS-B = 11 units CENP = 1 unit;<br>SCL-70 = 2 units;<br>Jo-1 = 0 units<br>Spec. component = 1 | EC4d = 15 units<br>BC4d = 50 units<br>CBCAPS component = 4.814 | =−5.2626 + 0.9877 × 2 + 4.814 + −2.4944 × 1 = −1.0<br>NON SUGGESTIVE |

It follows that equivocal results for the Index must be defined when ANA and/or the markers forming the specificity component are near the cutoff value (and therefore potentially able to affect the positivity or negativity of the index). We defined an equivocal ANA component when ANA levels ranged from 16 to 24 Units (20% CV at the 20 Units cutoff), or 48 to 72 units (20% CV at the 60 Units cutoff). Alternatively, we defined an equivocal antibody specificity component when anti-MCV levels ranged from 56 to 84 units (20% CV at the 70 Units cutoff), or when SSB-La, CENP, SCl-70 and Jo-1 ranged from 8 to 12 units (20% CV at the 10 Units cutoff).

As presented in Table 17 the change in the index value from positive to negative is also heavily dependent on the CBCAPS component in index equation. A decision rule based on equivocal results for the Index was established. Of the 794 subjects enrolled a total of 39 of them (4.9%) presented an equivocal result.

TABLE 17

Effects of CBCAPS component on Equivocal definition

|  | 16 < ANA units | 16 ≤ ANA ≤ 24 | 24 < ANA < 48 | 48 ≤ ANA ≤ 72 | ANA > 72 units |
|---|---|---|---|---|---|
| Specificity component = 0 | NOT EQUIVOCAL | Equivocal if CBCAPS component between 4.2749 and 5.2626 | NOT EQUIVOCAL | Equivocal if CBCAPS component between 3.2872 and 4.2749 | NOT EQUIVOCAL |
| Specificity component Equivocal | Equivocal if CBCAPS component between 5.2626 and 7.757 | Equivocal if CBCAPS component between 4.2749 and 7.757 | Equivocal if CBCAPS component between 4.2749 and 6.7693 | Equivocal if CBCAPS component between 3.2872 and 6.7693 | Equivocal if CBCAPS component between 3.2872 and 5.7816 |
| Specificity component = 1 | NOT EQUIVOCAL | Equivocal if CBCAPS component between 6.7693 and 7.757 | NOT EQUIVOCAL | Equivocal if CBCAPS component between 5.7816 and 6.7693 | NOT EQUIVOCAL |

Methods
FACS Measurements

C4d deposited on erythrocytes (EC4d) and B lymphocytes (BC4d) were measured using a validated FACS assay.

EC4d: whole blood (50 µl) was washed with Dulbecco's phosphate buffered saline, centrifuged for 5 minutes (800 g) and erythrocytes pellets were resuspended with 500 µl of 1% normal goat serum solution (Jackson Immunoresearch Laboratories, West Grove, Pa.). A 10 µl erythrocyte suspension was subsequently stained with purified mouse monoclonal antibodies against human C4d (mouse anti human C4d, Quidel inc, San Diego), or alternatively using non-specific mouse anti-human IgGI kappa antibody (MOPC-21, BD Biosciences, San Jose, Calif.) for 45 minutes at 4° C. Samples were then washed as described above. Erythrocyte pellets were re-suspended in a solution (25 µl) containing goat anti-mouse antibody conjugated to fluorescein isothiocyanate (FITC, Jackson ImmunoResearch Laboratories, West Grove, Pa.) for 45 minutes at 4° C. (in the dark). Following staining, washing and resuspension with 250 µL of cold 1% normal goat serum solution the erythrocytes were subjected to FACS analysis for detection of C4d deposited on cell surface.

BC4d levels: following lysis of erythrocytes from whole blood (700 µl) using ammonium chloride-based reagent (BD Pharm Lyse, BD Bioscience, San Jose, Calif.) and centrifugation (5 minutes at 800 g), cell pellets were resuspended in 500 µl of a 1% normal goat serum solution and stained using monoclonal C4d antibody (45 minutes at 2-8° C.) as described above. A 25 µl cell suspension was subsequently stained using purified mouse monoclonal antibodies against human C4d or non-specific mouse anti-human IgGI kappa antibody as above for 45 minutes at 4° C. Cell surface C4d staining was detected using goat anti-mouse fluorescein isothiocyanate (FITC) antibody (45 minutes at 2-8° C., dark). A monoclonal antibody against human CD-19 (CD-19 reacts with the 95 kDa type I transmembrane glycoprotein expressed during all stages of B-cell differentiation and maturation) conjugated to R-phycoerythrin (R-PE) was used to detect the C4d complement activation derived fragment specific to the B-lymphocytes.

All FACS analyses used a Beckman Coulter FC500 cytometer and CXP software (Beckman coulter, Brea Calif.). The mean fluorescence intensity (MFI) for the isotype background control and each complement protein (C4d) was obtained, and the net MFI was then determined by subtracting the non-specific MFI from the specific MFI results. Median inter-day (5 consecutive days) coefficient of variations for EC4d levels at low, medium and high intensity was established using blood from 44 patients with rheumatic diseases and ranged from 3.3 to 9.6% for EC4d. For BC4D inter-day coefficient of variations at low, medium and high intensity in 34 patients with rheumatic diseases ranged from 5.3 to 12.1%. In all FACS experiments controls establishing proper calibration, compensation and linearity of the flow cytometer were included.

ELISA Measurements for ANA, dsDNA and antiMCV

ANA, anti-dsDNA and antimutated citrullinated vimentin antibodies [anti-MCV, an anticitrullinated peptide antibody](16) were measured using enzyme linked immunosorbent assays (ELISA). All ELISA methods used have been cleared by the US Food and Drug Administration as safe and effective for in vitro diagnostic uses. ANA and anti-dsDNA were from INOVA Diagnostics (INOVA, San Diego, Calif.) and anti-MCV was from Orgentec Diagnostika, Germany). Intra-day and inter-day coefficient of variations for all methods were established in our clinical laboratory and were below 20%. For all ELISA experiments appropriate positive and negative controls were included.

Fluoroenzymatic immunoassays measurements for CENP, Jo-1, La/SS-B, Ro/SS-A, SCl-70, Smith.

The qualitative measurement of SS-A/Ro (60 kDa, 52 kDa), SS-B/La, Centromere B (CENP), Scl-70 (anti-topoisomerase I), Jo-1, and Smith antinuclear IgG antibodies in serum or plasma were performed using the EliA IgG method on the Phadia 250 instrument (ThermoFisher, Uppsala, Sweden). For each analyte, the cutoffs recommended by the manufacturer were used. Analytical repeatability and reproducibility was lower than 20% for all analytes in our clinical laboratory.

Statistical Analysis

Statistical analysis was conducted using the R software version 2.15.0. Receiver operating curves were used as appropriate for each of the markers (univariate analysis) and also following the determination of an index value as the output of multivariate logistic regression equation. As measures of performance, sensitivity and specificity (1—false positives rate) were computed. The reported performance statistics (sensitivity, specificity), ROC AUC) were calculated using k-fold cross validation (with k=10), repeated 10 times (reported results are averages). In addition, performance characteristics were computed with three other validation methods (data not shown), all with very similar results to the reported performance characteristics. The three additional validation methods were leave-one-out cross validation, average of split-sample validation (with two thirds for training, one third for validation), and apparent validation (also known as re-substitution). Where applicable, validation sets were generated with stratification by disease ((Book) Clinical Prediction Models: A Practical Approach to Development, Validation and Updating. Ewout W. Steyerberg. 2009)

REFERENCES (1) Rahman A, Isenberg D A. Systemic lupus erythematosus. N Engl J Med 2008; 358(9):929-939.
(2) Helmick C G, Felson D T, Lawrence R C, Gabriel S, Hirsch R, Kwoh C K et al. Estimates of the prevalence of arthritis and other rheumatic conditions in the United States. Part I. Arthritis Rheum 2008; 58(1):15-25.
(3) Bastian H M, Roseman J M, McGwin G, Jr., Alarcon G S, Friedman A W, Fessler B J et al. Systemic lupus erythematosus in three ethnic groups. XII. Risk factors for lupus nephritis after diagnosis. Lupus 2002; 11(3): 152-160.
(4) Tan E M, Cohen A S, Fries J F, Masi A T, McShane D J, Rothfield N F et al. The 1982 revised criteria for the classification of systemic lupus erythematosus. Arthritis Rheum 1982; 25(11):1271-1277.
(5) Smith E L, Shmerling R H. The American College of Rheumatology criteria for the classification of systemic lupus erythematosus: strengths, weaknesses, and opportunities for improvement. Lupus 1999; 8(8):586-595.
(6) Egner W. The use of laboratory tests in the diagnosis of SLE. J Clin Pathol 2000; 53(6):424-432.
(7) Manderson A P, Botto M, Walport M J. The role of complement in the development of systemic lupus erythematosus. Annu Rev Immunol 2004; 22:431-456.
(8) Manzi S, Navratil J S, Ruffing M J, Liu C C, Danchenko N, Nilson S E et al. Measurement of erythrocyte C4d and complement receptor 1 in systemic lupus erythematosus. Arthritis Rheum 2004; 50(11):3596-3604.
(9) Navratil J S, Manzi S, Kao A H, Krishnaswami S, Liu C C, Ruffing M J et al. Platelet C4d is highly specific for systemic lupus erythematosus. Arthritis Rheum 2006; 54(2):670-674.
(10) Yang D H, Chang D M, Lai J H, Lin F H, Chen C H. Usefulness of erythrocyte-bound C4d as a biomarker to predict disease activity in patients with systemic lupus erythematosus. Rheumatology (Oxford) 2009; 48(9): 1083-1087.
(11) Liu C C, Kao A H, Hawkins D M, Manzi S, Sattar A, Wilson N et al. Lymphocyte-bound complement activation products as biomarkers for diagnosis of systemic lupus erythematosus. Clin Transl Sci 2009; 2(4):300-308.
(12) Kao A H, Navratil J S, Ruffing M J, Liu cc, Hawkins D, Mc kinnon K M et al. Erythrocyte C3d and C4d for monitoring disease activity in systemic lupus erythematosus. Arthritis and Rheumatism 62[3], 837-844. 2010.
(13) Batal I, Liang K, Bastacky S, Kiss L P, McHale T, Wilson N L et al. Prospective assessment of C4d deposits on circulating cells and renal tissues in lupus nephritis: a pilot study. Lupus 21[1], 13-26. 2012.
(14) Kalunian K C, Chatham W W, Massarotti E M, Reyes-Thomas J, Harris C, Furie R A et al. Measurements of cell bound complement activation products enhance diagnostic performance in systemic lupus erythematosus. Arthritis Rheum 2012.
(15) Singh V, Mahoney J A, Petri M. Erythrocyte C4d and complement receptor 1 in systemic lupus erythematosus. J Rheumatol 2008; 35(10): 1989-1993.
(16) Bang H, Egerer K, Gauliard A, Luthke K, Rudolph P E, Fredenhagen G et al. Mutation and citrullination modifies vimentin to a novel autoantigen for rheumatoid arthritis. Arthritis Rheum 2007; 56(8):2503-2511.
(17) Steyerberg E, Ewout W. Clinical prediction models: a practical approach to development, validation and updating. 2009. Springer-Verlag.

We claim:

1. A method of treating systemic lupus erythematosus (SLE) in a subject identified as having SLE based on a systemic lupus erythematosus risk score, the method comprising:

(A) determining a level of erythrocyte C4d marker, a level of B-cell C4d marker, a level of anti-nuclear antibody, a level of anti-Sjögren's syndrome type B antigen antibody, a level of anti-Scl-70 antibody, a level of anti-Jo-1 antibody, and a level of anti-centromere protein B antibody in a blood sample from the subject;

(B) calculating a systemic lupus erythematosus index score with the level of the erythrocyte C4d marker, the level of the B-cell C4d marker, the level of the anti-nuclear antibody, the level of anti-Sjögren's syndrome type B antigen antibody, the level of anti-Scl-70 antibody, the level of anti-Jo-1 antibody, and the level of anti-centromere protein B antibody with the equation:

$$\text{Index}=-5.2626+0.9877\times ANAComp+[0.2955\times \log(EC4d)+1.0260\times \log(BC4d)]-2.4944\times SpecComp;$$

wherein:

(i) Index is the systemic lupus erythematosus index score;

(ii) ANAComp is:

(a) 0, when the level of anti-nuclear antibody <20 units, as measured by an enzyme-linked immunosorbent assay;

(b) 1, when the level of anti-nuclear antibody is ≥20 units and <60 units, as measured by an enzyme-linked immunosorbent assay; or (c) 2, when the level of anti-nuclear antibody ≥60 units, as measured by an enzyme-linked immunosorbent assay;

(iii) log is natural log;

(iv) EC4d is net mean fluorescence intensity of erythrocyte C4d marker, as measured by fluorescence activated flow cytometry;

(v) BC4d is net mean fluorescence intensity of B-cell C4d marker, as measured by fluorescence activated flow cytometry; and (vi) SpecComp is:

(a) 0, when the level of anti-Sjögren's syndrome type B antigen antibody is ≤10 Units/mL; the level of anti-Scl-70 antibody is ≤10 Units/mL; the level of anti-Jo-1 antibody is ≤10 Units/mL; and the level of anti-centromere protein B antibody is ≤10 Units/mL; where each are as measured by a fluoroenzymatic immunoassay;
(b) 1, when one or more of the level of anti-Sjögren's syndrome type B antigen antibody is >10 Units/mL; the level of anti-Scl-70 antibody >10 Units/mL; the level of anti-Jo-1 antibody is >10 Units/mL; or the level of anti-centromere protein B antibody is >10 Units/mL; where each are as measured by a fluoroenzymatic immunoassay;
(C) identifying the subject as having SLE when the index score is >0; and
(D) treating the subject identified as having SLE in step (C) with an effective amount of belimumab.

2. A method of treating systemic lupus erythematosus (SLE) in a subject identified as having SLE based on a systemic lupus erythematosus risk score, the method comprising:
(A) determining a level of erythrocyte C4d marker, a level of B-cell C4d marker, a level of anti-nuclear antibody, a level of anti-Sjögren's syndrome type B antigen antibody, a level of anti-Scl-70 antibody, a level of anti-Jo-1 antibody, and a level of anti-centromere protein B antibody in a blood sample from the subject;
(B) calculating a systemic lupus erythematosus index score with the level of the erythrocyte C4d marker, the level of the B-cell C4d marker, the level of the anti-nuclear antibody, the level of anti-Sjögren's syndrome type B antigen antibody, the level of anti-Scl-70 antibody, the level of anti-Jo-1 antibody, and the level of anti-centromere protein B antibody with the equation:

$$Index = -5.2626 + 0.9877 \times ANAComp[0.2955 \times \log(EC4d) + 1.0260 \times \log(BC4d)] - 2.4944 \times SpecComp;$$

wherein:
(i) Index is the systemic lupus erythematosus index score;
(ii) ANAComp is:
  (a) 0, when the level of anti-nuclear antibody <20 units, as measured by an enzyme-linked immunosorbent assay;
  (b) 1, when the level of anti-nuclear antibody is ≥20 units and <60 units, as measured by an enzyme-linked immunosorbent assay; or
  (c) 2, when the level of anti-nuclear antibody ≥60 units, as measured by an enzyme-linked immunosorbent assay;
(iii) log is natural log;
(iv) EC4d is net mean fluorescence intensity of erythrocyte C4d marker, as measured by fluorescence activated flow cytometry;
(v) BC4d is net mean fluorescence intensity of B-cell C4d marker, as measured by fluorescence activated flow cytometry; and
(vi) SpecComp is:
  (a) 0, when the level of anti-Sjögren's syndrome type B antigen antibody is ≤10 Units/mL; the level of anti-Scl-70 antibody is ≤10 Units/mL; the level of anti-Jo-1 antibody is ≤10 Units/mL; and the level of anti-centromere protein B antibody is ≤10 Units/mL; where each are as measured by a fluoroenzymatic immunoassay;
  (b) 1, when one or more of the level of anti-Sjögren's syndrome type B antigen antibody is >10 Units/mL; the level of anti-Scl-70 antibody >10 Units/mL; the level of anti-Jo-1 antibody is >10 Units/mL; or the level of anti-centromere protein B antibody is >Units/mL; where each are as measured by a fluoroenzymatic immunoassay;
(C) identifying the subject as having SLE when the index score is >0; and
(D) treating the subject identified as having SLE in step (C) with an effective amount of cyclophosphami de.

3. A method of treating systemic lupus erythematosus (SLE) in a subject identified as having SLE based on a systemic lupus erythematosus risk score, the method comprising:
(A) determining a level of erythrocyte C4d marker, a level of B-cell C4d marker, a level of anti-nuclear antibody, a level of anti-Sjögren's syndrome type B antigen antibody, a level of anti-Scl-70 antibody, a level of anti-Jo-1 antibody, and a level of anti-centromere protein B antibody in a blood sample from the subject;
(B) calculating a systemic lupus erythematosus index score with the level of the erythrocyte C4d marker, the level of the B-cell C4d marker, the level of the anti-nuclear antibody, the level of anti-Sjögren's syndrome type B antigen antibody, the level of anti-Scl-70 antibody, the level of anti-Jo-1 antibody, and the level of anti-centromere protein B antibody with the equation:

$$Index = -5.2626 + 0.9877 \times ANAComp[0.2955 \times \log(EC4d) + 1.0260 \times \log(BC4d)] - 2.4944 \times SpecComp;$$

wherein:
(i) Index is the systemic lupus erythematosus index score;
(ii) ANAComp is:
  (a) 0, when the level of anti-nuclear antibody <20 units, as measured by an enzyme-linked immunosorbent assay;
  (b) 1, when the level of anti-nuclear antibody is ≥20 units and <60 units, as measured by an enzyme-linked immunosorbent assay; or
  (c) 2, when the level of anti-nuclear antibody ≥60 units, as measured by an enzyme-linked immunosorbent assay;
(iii) log is natural log;
(iv) EC4d is net mean fluorescence intensity of erythrocyte C4d marker, as measured by fluorescence activated flow cytometry;
(v) BC4d is net mean fluorescence intensity of B-cell C4d marker, as measured by fluorescence activated flow cytometry; and
(vi) SpecComp is:
  (a) 0, when the level of anti-Sjögren's syndrome type B antigen antibody is ≤10 Units/mL; the level of anti-Scl-70 antibody is ≤10 Units/mL; the level of anti-Jo-1 antibody is ≤10 Units/mL; and the level of anti-centromere protein B antibody is ≤10 Units/mL; where each are as measured by a fluoroenzymatic immunoassay;
  (b) 1, when one or more of the level of anti-Sjögren's syndrome type B antigen antibody is >10 Units/mL; the level of anti-Scl-70 antibody >10 Units/mL; the level of anti-Jo-1 antibody is >10 Units/mL; or the level of anti-centromere protein B antibody is >10 Units/mL; where each are as measured by a fluoroenzymatic immunoassay;
(C) identifying the subject as having SLE when the index score is >0; and
(D) treating the subject identified as having SLE in step (C) with an effective amount of methotrexate.

4. A method of treating systemic lupus erythematosus (SLE) in a subject identified as having SLE based on a systemic lupus erythematosus risk score, the method comprising:
  (A) determining a level of erythrocyte C4d marker, a level of B-cell C4d marker, a level of anti-nuclear antibody, a level of anti-Sjögren's syndrome type B antigen antibody, a level of anti-Scl-70 antibody, a level of anti-Jo-1 antibody, and a level of anti-centromere protein B antibody in a blood sample from the subject;
  (B) calculating a systemic lupus erythematosus index score with the level of the erythrocyte C4d marker, the level of the B-cell C4d marker, the level of the anti-nuclear antibody, the level of anti-Sjögren's syndrome type B antigen antibody, the level of anti-Scl-70 antibody, the level of anti-Jo-1 antibody, and the level of anti-centromere protein B antibody with the equation:

$$Index = -5.2626 + 0.9877 \times ANAComp[0.2955 \times \log(EC4d) + 1.0260 \times \log(BC4d)] - 2.4944 \times SpecComp;$$

wherein:
  (i) Index is the systemic lupus erythematosus index score;
  (ii) ANAComp is:
    (a) 0, when the level of anti-nuclear antibody <20 units, as measured by an enzyme-linked immunosorbent assay;
    (b) 1, when the level of anti-nuclear antibody is ≥20 units and <60 units, as measured by an enzyme-linked immunosorbent assay; or
    (c) 2, when the level of anti-nuclear antibody ≥60 units, as measured by an enzyme-linked immunosorbent assay;
  (iii) log is natural log;
  (iv) EC4d is net mean fluorescence intensity of erythrocyte C4d marker, as measured by fluorescence activated flow cytometry;
  (v) BC4d is net mean fluorescence intensity of B-cell C4d marker, as measured by fluorescence activated flow cytometry; and
  (vi) SpecComp is:
    (a) 0, when the level of anti-Sjögren's syndrome type B antigen antibody is ≤10 Units/mL; the level of anti-Scl-70 antibody is ≤10 Units/mL; the level of anti-Jo-1 antibody is ≤10 Units/mL; and the level of anti-centromere protein B antibody is ≤10 Units/mL; where each are as measured by a fluoroenzymatic immunoassay;
    (b) 1, when one or more of the level of anti-Sjögren's syndrome type B antigen antibody is >10 Units/mL; the level of anti-Scl-70 antibody >10 Units/mL; the level of anti-Jo-1 antibody is >10 Units/mL; or the level of anti-centromere protein B antibody is >10 Units/mL; where each are as measured by a fluoroenzymatic immunoassay;
  (C) identifying the subject as having SLE when the index score is >0; and
  (D) treating the subject identified as having SLE in step (C) with an effective amount of azathioprine.

5. A method of treating systemic lupus erythematosus (SLE) in a subject identified as having SLE based on a systemic lupus erythematosus risk score, the method comprising:
  (A) determining a level of erythrocyte C4d marker, a level of B-cell C4d marker, a level of anti-nuclear antibody, a level of anti-Sjögren's syndrome type B antigen antibody, a level of anti-Scl-70 antibody, a level of anti-Jo-1 antibody, and a level of anti-centromere protein B antibody in a blood sample from the subject;
  (B) calculating a systemic lupus erythematosus index score with the level of the erythrocyte C4d marker, the level of the B-cell C4d marker, the level of the anti-nuclear antibody, the level of anti-Sjögren's syndrome type B antigen antibody, the level of anti-Scl-70 antibody, the level of anti-Jo-1 antibody, and the level of anti-centromere protein B antibody with the equation:

$$Index = -5.2626 + 0.9877 \times ANAComp[0.2955 \times \log(EC4d) + 1.0260 \times \log(BC4d)] - 2.4944 \times SpecComp;$$

wherein:
  (i) Index is the systemic lupus erythematosus index score;
  (ii) ANAComp is:
    (a) 0, when the level of anti-nuclear antibody <20 units, as measured by an enzyme-linked immunosorbent assay;
    (b) 1, when the level of anti-nuclear antibody is ≥20 units and <60 units, as measured by an enzyme-linked immunosorbent assay; or
    (c) 2, when the level of anti-nuclear antibody ≥60 units, as measured by an enzyme-linked immunosorbent assay;
  (iii) log is natural log;
  (iv) EC4d is net mean fluorescence intensity of erythrocyte C4d marker, as measured by fluorescence activated flow cytometry;
  (v) BC4d is net mean fluorescence intensity of B-cell C4d marker, as measured by fluorescence activated flow cytometry; and
  (vi) SpecComp is:
    (a) 0, when the level of anti-Sjögren's syndrome type B antigen antibody is ≤10 Units/mL; the level of anti-Scl-70 antibody is ≤10 Units/mL; the level of anti-Jo-1 antibody is ≤10 Units/mL; and the level of anti-centromere protein B antibody is ≤10 Units/mL; where each are as measured by a fluoroenzymatic immunoassay;
    (b) 1, when one or more of the level of anti-Sjögren's syndrome type B antigen antibody is >10 Units/mL; the level of anti-Scl-70 antibody >10 Units/mL; the level of anti-Jo-1 antibody is >10 Units/mL; or the level of anti-centromere protein B antibody is >10 Units/mL; where each are as measured by a fluoroenzymatic immunoassay;
  (C) identifying the subject as having SLE when the index score is >0; and
  (D) treating the subject identified as having SLE in step (C) with an effective amount of leflunomide.

6. A method of treating systemic lupus erythematosus (SLE) in a subject identified as having SLE based on a systemic lupus erythematosus risk score, the method comprising:
  (A) determining a level of erythrocyte C4d marker, a level of B-cell C4d marker, a level of anti-nuclear antibody, a level of anti-Sjögren's syndrome type B antigen antibody, a level of anti-Scl-70 antibody, a level of anti-Jo-1 antibody, and a level of anti-centromere protein B antibody in a blood sample from the subject;
  (B) calculating a systemic lupus erythematosus index score with the level of the erythrocyte C4d marker, the level of the B-cell C4d marker, the level of the anti-nuclear antibody, the level of anti-Sjögren's syndrome type B antigen antibody, the level of anti-Scl-70 antibody, the level of anti-Jo-1 antibody, and the level of anti-centromere protein B antibody with the equation:

Index=−5.2626+0.9877×*ANAComp*[0.2955×log(*EC4d*)+1.0260×log(*BC4d*)]−2.4944×*SpecComp*;

wherein:
(i) Index is the systemic lupus erythematosus index score;
(ii) ANAComp is:
  (a) 0, when the level of anti-nuclear antibody <20 units, as measured by an enzyme-linked immunosorbent assay;
  (b) 1, when the level of anti-nuclear antibody is ≥20 units and <60 units, as measured by an enzyme-linked immunosorbent assay; or
  (c) 2, when the level of anti-nuclear antibody ≥60 units, as measured by an enzyme-linked immunosorbent assay;
(iii) log is natural log;
(iv) EC4d is net mean fluorescence intensity of erythrocyte C4d marker, as measured by fluorescence activated flow cytometry;
(v) BC4d is net mean fluorescence intensity of B-cell C4d marker, as measured by fluorescence activated flow cytometry; and
(vi) SpecComp is:
  (a) 0, when the level of anti-Sjögren's syndrome type B antigen antibody is ≤10 Units/mL; the level of anti-Scl-70 antibody is ≤10 Units/mL; the level of anti-Jo-1 antibody is ≤10 Units/mL; and the level of anti-centromere protein B antibody is ≤10 Units/mL; where each are as measured by a fluoroenzymatic immunoassay;
  (b) 1, when one or more of the level of anti-Sjögren's syndrome type B antigen antibody is >10 Units/mL; the level of anti-Scl-70 antibody >10 Units/mL; the level of anti-Jo-1 antibody is >10 Units/mL; or the level of anti-centromere protein B antibody is >Units/mL; where each are as measured by a fluoroenzymatic immunoassay;
(C) identifying the subject as having SLE when the index score is >0; and
(D) treating the subject identified as having SLE in step (C) with an effective amount of hydroxychloroquine.

7. A method of treating systemic lupus erythematosus (SLE) in a subject identified as having SLE, the method comprising:
(A) determining a level of erythrocyte C4d marker, a level of B-cell C4d marker, a level of anti-nuclear antibody, a level of Sjögren's syndrome type B antigen, a level of Scl-70 antibody, a level of Jo-1 antibody, and a level of centromere B protein in a blood sample from the subject;
(B) calculating a systemic lupus erythematosus index score with the levels of erythrocyte C4d marker, B-cell C4d marker, anti-nuclear antibody, Sjögren's syndrome type B antigen, Scl-70 antibody, Jo-1 antibody, and centromere B protein with the equation:

Index=−5.2626+0.9877×*ANAComp*[0.2955×log(*EC4d*)+1.0260×log(*BC4d*)]−2.4944×*SpecComp*;

wherein:
(i) Index is the systemic lupus erythematosus index score;
(ii) ANAComp is:
  (a) 0, when the level of anti-nuclear antibody <20 units, as measured by an enzyme-linked immunosorbent assay;
  (b) 1, when the level of anti-nuclear antibody is ≥20 units and <60 units, as measured by an enzyme-linked immunosorbent assay; or
  (c) 2, when the level of anti-nuclear antibody ≥60 units, as measured by an enzyme-linkedimmunosorbent assay;
(iii) log is natural log;
(iv) EC4d is net mean fluorescence intensity of erythrocyte C4d marker, as measured by fluorescence activated flow cytometry;
(v) BC4d is net mean fluorescence intensity of B-cell C4d marker, as measured by fluorescence activated flow cytometry; and
(vi) SpecComp is:
  (a) 0, when the level of Sjögren's syndrome type B antigen is ≤10 Units/mL; the level of Scl-70 antibody is ≤10 Units/mL; the level of Jo-1 antibody is ≤10 Units/mL; and the level of centromere B protein is ≤10 Units/mL; where each are as measured by a fluoroenzymatic immunoassay;
  (b) 1, when one or more of the level of Sjögren's syndrome type B antigen is >10 Units/mL; the level of Scl-70 antibody >10 Units/mL; the level of Jo-1 antibody is >10 Units/mL; or the level of centromere B protein is >10 Units/mL; where each are as measured by a fluoroenzymatic immunoassay;
(C) identifying the subject as having SLE when the index score is >0; and
(D) treating the subject identified as having SLE in step (C) with an effective amount of a corticosteroid.

8. The method of claim 1, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

9. The method of claim 2, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

10. The method of claim 3, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

11. The method of claim 4, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

12. The method of claim 5, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

13. The method of claim 6, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

14. The method of claim 7, wherein determining the level of erythrocyte C4d marker comprises determining the level of erythrocyte C4d on the surface of erythrocytes, and wherein determining the level of B-cell C4d marker comprises determining the level of B-cell C4d on the surface of B lymphocytes.

\* \* \* \* \*